US011666745B2

(12) United States Patent
Moss et al.

(10) Patent No.: US 11,666,745 B2
(45) Date of Patent: Jun. 6, 2023

(54) ROTARY VALVES FOR MANAGING FLUID FLOWS IN MEDICAL SYSTEMS

(71) Applicant: Fresenius Medical Care Holdings, Inc., Waltham, MA (US)

(72) Inventors: Jon F. Moss, Antioch, CA (US); Bert D. Egley, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 681 days.

(21) Appl. No.: 16/662,601

(22) Filed: Oct. 24, 2019

(65) Prior Publication Data
US 2020/0179674 A1   Jun. 11, 2020

Related U.S. Application Data

(60) Provisional application No. 62/776,588, filed on Dec. 7, 2018.

(51) Int. Cl.
*A61M 39/22* (2006.01)
*A61M 39/24* (2006.01)
(Continued)

(52) U.S. Cl.
CPC .......... *A61M 39/24* (2013.01); *A61M 1/1656* (2013.01); *A61M 1/267* (2014.02);
(Continued)

(58) Field of Classification Search
CPC .................. A61M 39/24; A61M 1/267; A61M 2039/226; A61M 2039/242;
(Continued)

(56) References Cited

U.S. PATENT DOCUMENTS 2,530,581 A   11/1950   Markis et al.
3,973,683 A   8/1976   Keller
(Continued)

FOREIGN PATENT DOCUMENTS

CN   108367147   8/2018
EP   1509261   3/2005
(Continued)

OTHER PUBLICATIONS

International Search Report and Written Opinion in Application No. PCT/US2019/042967, dated Oct. 8, 2019, 11 pages.
(Continued)

*Primary Examiner* — Marina A Tietjen
(74) *Attorney, Agent, or Firm* — Fish & Richardson P.C.

(57) ABSTRACT

In one aspect, a valve includes a valve body rotatable about a central axis of the valve body, an interior channel adjacent the valve body for permitting a fluid to flow through an axial opening of the interior channel, and a plug within the interior channel that is movable between a first axial position at the axial opening and a second axial position spaced apart from the axial opening. In the first axial position, the plug closes the axial opening to prevent the fluid from flowing through the axial opening in a first direction and to prevent the fluid from flowing through the axial opening in a second direction that is opposite to the first direction. In the second axial position, the plug permits the fluid to flow through the axial opening into the interior channel in the first direction.

17 Claims, 13 Drawing Sheets

(51) Int. Cl.
*A61M 1/16* (2006.01)
*A61M 1/28* (2006.01)
*F16K 5/04* (2006.01)
*A61M 1/26* (2006.01)
*F16K 1/14* (2006.01)

(52) U.S. Cl.
CPC ............ *A61M 1/28* (2013.01); *A61M 39/223* (2013.01); *F16K 1/14* (2013.01); *F16K 5/04* (2013.01); *A61M 2039/226* (2013.01); *A61M 2039/229* (2013.01); *A61M 2039/242* (2013.01); *A61M 2039/248* (2013.01); *A61M 2039/2473* (2013.01); *A61M 2039/2493* (2013.01); *A61M 2205/128* (2013.01)

(58) Field of Classification Search
CPC .. A61M 2039/2473; A61M 2039/2493; A61M 2039/229; A61M 2039/248; A61M 1/1656; A61M 1/28; A61M 39/223; A61M 2205/128; F16K 1/14; F16K 5/04; F16K 11/08–0876; F16K 15/044; F16K 2200/304; F16K 31/52425; F16K 31/52458–52466
See application file for complete search history.

(56) References Cited

U.S. PATENT DOCUMENTS

| | | | |
|---|---|---|---|
| 4,001,556 A | 1/1977 | Folchi et al. | |
| 4,229,136 A | 10/1980 | Panissidi | |
| 4,274,802 A | 6/1981 | Inaba et al. | |
| 4,363,585 A | 12/1982 | Keller et al. | |
| 4,687,941 A | 8/1987 | Laserberg et al. | |
| 5,111,997 A | 5/1992 | Ikuta et al. | |
| 5,540,668 A | 7/1996 | Wilson, Jr. | |
| 5,622,468 A | 4/1997 | Viollet | |
| 6,939,111 B2 | 9/2005 | Huitt et al. | |
| 7,162,884 B2 | 1/2007 | Alles | |
| 7,216,672 B1 | 5/2007 | Chen | |
| 8,555,926 B2 | 10/2013 | MacDuff et al. | |
| 9,827,361 B2 | 11/2017 | Pudil et al. | |
| 9,931,447 B2 | 4/2018 | Layser et al. | |
| 10,058,694 B2 | 8/2018 | Norris et al. | |
| 10,918,850 B2 | 2/2021 | Oerter | |
| 2003/0098270 A1 | 5/2003 | Thompson | |
| 2004/0221904 A1 | 11/2004 | Usher et al. | |
| 2005/0274658 A1 | 12/2005 | Rosenbaum et al. | |
| 2007/0272311 A1* | 11/2007 | Trocki | A61M 39/223 137/601.2 |
| 2008/0172006 A1* | 7/2008 | Hicks | A61M 39/24 604/249 |
| 2008/0214979 A1 | 9/2008 | Brugger | |
| 2010/0198129 A1 | 8/2010 | Stemby | |
| 2010/0312174 A1 | 12/2010 | Hoffman | |
| 2010/0326531 A1* | 12/2010 | Oltman | F16K 5/0605 251/366 |
| 2012/0193563 A1* | 8/2012 | Croci | F16K 15/1848 251/231 |
| 2014/0088482 A1 | 3/2014 | Schlaeper | |
| 2014/0097371 A1 | 4/2014 | Huynh | |
| 2015/0219230 A1 | 8/2015 | Muennich | |
| 2015/0343127 A1 | 12/2015 | Childers et al. | |
| 2016/0008529 A1 | 1/2016 | Hoffman | |
| 2016/0058995 A1* | 3/2016 | Schriver | A61M 39/24 604/67 |
| 2016/0239025 A1 | 8/2016 | Van Der Merwe et al. | |
| 2017/0106131 A1 | 4/2017 | Hornig | |
| 2017/0189598 A1 | 7/2017 | Slade | |
| 2018/0229021 A1 | 8/2018 | Donlon et al. | |
| 2019/0134289 A1 | 5/2019 | Pudil et al. | |
| 2020/0030518 A1 | 1/2020 | Brugger | |
| 2020/0033897 A1 | 1/2020 | Jensen et al. | |
| 2020/0041021 A1 | 2/2020 | Moss et al. | |
| 2020/0271232 A1 | 8/2020 | Nakagami | |
| 2021/0299340 A1 | 9/2021 | Adams et al. | |
| 2021/0341073 A1 | 11/2021 | Moss et al. | |

FOREIGN PATENT DOCUMENTS

| | | |
|---|---|---|
| EP | 2694127 | 2/2014 |
| EP | 2931331 | 3/2018 |
| GB | 2458572 | 9/2009 |
| WO | WO 2002/043859 | 6/2002 |
| WO | WO 02/090671 | 11/2002 |
| WO | WO 2003/099355 | 12/2003 |
| WO | WO 2009/064984 | 5/2009 |
| WO | WO 2011/017215 | 2/2011 |

OTHER PUBLICATIONS

Invitation to Pay Additional Fees in International Application No. PCT/US2019/057775, dated Feb. 11, 2020, 11 pages.
PCT International Search Report and Written Opinion in International Appln. No. PCT/US2019/057775, dated Apr. 2, 2020, 17 pages.
PCT International Preliminary Report on Patentability in International Appln. No. PCT/US2019/042967, dated Feb. 11, 2021, 7 pages.
International Preliminary Report on Patentability in International Appln. No. PCT/US2019/043023, dated Feb. 11, 2021, 7 pages.
International Preliminary Report on Patentability in International Appln. No. PCT/US2019/0443 06, dated Feb. 11, 2021, 8 pages.
International Preliminary Report on Patentability in International Appln. No. PCT/US2020/044751, dated Feb. 17, 2022, 11 pages.
International Search Report and Written Opinion in International Appln. No. PCT/US2019/043023, dated Oct. 8, 2019, 9 pages.
International Search Report and Written Opinion in International Appln. No. PCT/US2019/044306, dated Oct. 24, 2019, 13 pages.
International Search Report and Written Opinion in International Appln. No. PCT/US2020/044751, dated Nov. 4, 2020, 18 pages.
PCT International Preliminary Report on Patentability in International Appln. No. PCT/US2019/057775, dated Jun. 17, 2021, 9 pages.

* cited by examiner

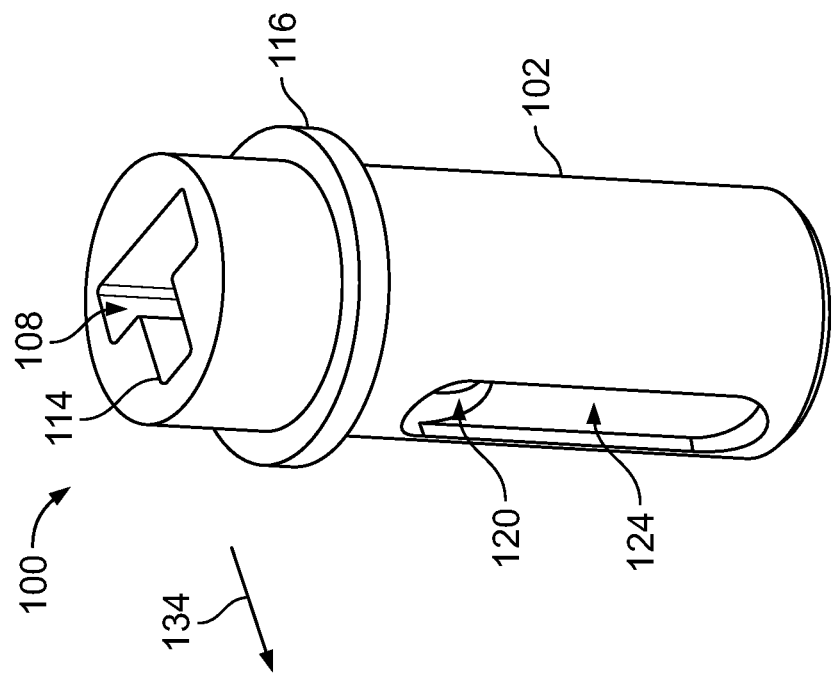
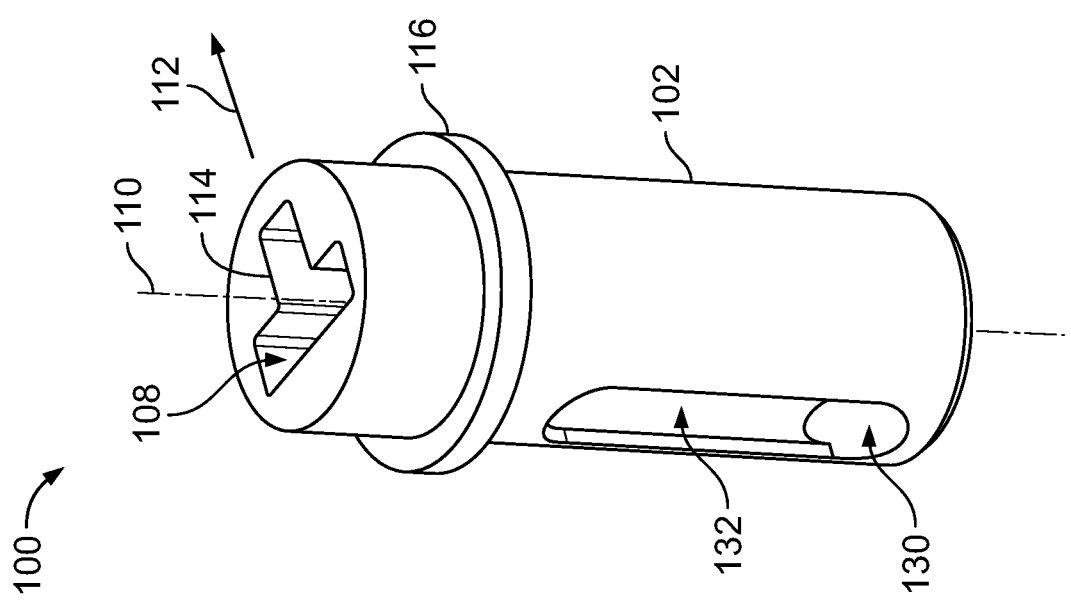

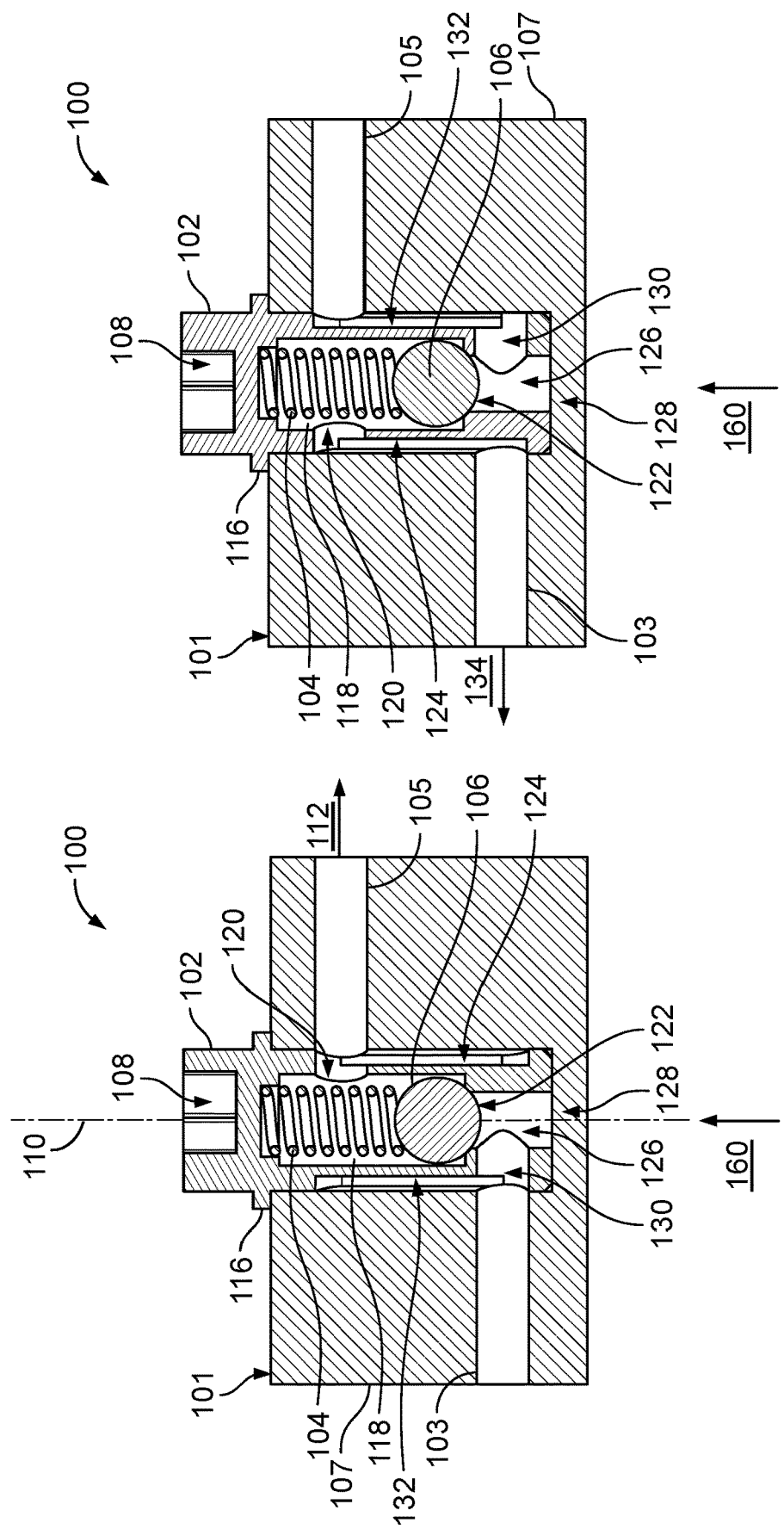

ROTARY VALVES FOR MANAGING FLUID FLOWS IN MEDICAL SYSTEMS

CROSS-REFERENCE TO RELATED APPLICATIONS

This application claims priority to U.S. Provisional Patent Application No. 62/776,588, filed on Dec. 7, 2018, the entire contents of which are incorporated herein by reference.

TECHNICAL FIELD

This disclosure relates to rotary valves for managing fluid flows in medical systems, such as fluid flows in dialysis systems.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal lateral channel is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home, usually overnight without clinical staff in attendance. This process is termed continuous cycler-assisted PD (CCPD). Many PD cyclers are designed to automatically infuse, dwell, and drain dialysate to and from the patient's peritoneal lateral channel. The treatment typically lasts for several hours, often beginning with an initial drain cycle to empty the peritoneal lateral channel of used or spent dialysate. The sequence then proceeds through the succession of fill, dwell, and drain phases that follow one after the other.

Various fluid paths within a dialysis system must be managed throughout a dialysis treatment via actuation of valves along the fluid paths.

SUMMARY

This disclosure relates to rotary valves for managing fluid flows in medical systems, such as fluid flows in dialysis systems.

In one aspect, a valve includes a valve body rotatable about a central axis of the valve body, an interior channel adjacent the valve body for permitting a fluid to flow through an axial opening of the interior channel, and a plug within the interior channel that is movable between a first axial position at the axial opening and a second axial position spaced apart from the axial opening. In the first axial position, the plug closes the axial opening to prevent the fluid from flowing through the axial opening in a first direction and to prevent the fluid from flowing through the axial opening in a second direction that is opposite to the first direction. In the second axial position, the plug permits the fluid to flow through the axial opening into the interior channel in the first direction.

Embodiments may include one or more of the following features.

In some embodiments, the valve further includes a compressible member within the interior channel that biases the plug to the first axial position.

In certain embodiments, the valve body defines a cam positioned adjacent the interior channel.

In some embodiments, the valve body is rotatable to a first rotational position in which a protrusion of the cam is aligned with and squeezes the compressible member into a compressed configuration that exerts a first cracking pressure on the plug, and a second rotational position in which the protrusion of the cam is aligned with and spaced apart from the compressible member to release the compressible member into an extended configuration that exerts a second cracking pressure on the plug, the second cracking pressure being less than the first cracking pressure.

In certain embodiments, the interior channel is a first interior channel, the compressible member is a first compressible member, and the valve further includes a second interior channel and a second compressible member carried therein, the second interior channel and the second compressible member positioned adjacent the plug and opposite the first interior channel and the first compressible member.

In some embodiments, the valve body is rotatable to a first rotational position in which a protrusion of the cam is aligned with and squeezes the first compressible member into a compressed configuration that biases the plug to the first axial position, and a second rotational position in which the protrusion of the cam is aligned with and spaced apart from the first compressible member to release the first and second compressible members into an extended configuration in which the second compressible member positions the plug at the second axial position to allow the fluid to flow through the axial opening in the first direction or to allow the fluid to flow through the axial opening and past the plug in the second direction.

In certain embodiments, the valve is configured such that the plug is movable from the first axial position to the second axial position by a pressure of the fluid flowing into the axial opening.

In some embodiments, the valve defines a lateral opening in the interior channel through which fluid can flow out of the interior channel.

In certain embodiments, the valve body defines a first exterior channel along a first side of the valve body and a second exterior channel along a second side of the valve body that is opposite the first side, the first and second exterior channels being in fluid communication with the interior channel.

In some embodiments, the valve body is rotatable to a first rotational position in which the fluid flows in a third direction across the valve body and past the first and second exterior channels and a second rotational position in which the fluid flows in a fourth direction across the valve body and along the first and second exterior channels, the fourth direction being opposite to the third direction.

In another aspect, a valve includes an interior channel for permitting a fluid to flow through the valve and an opening to the interior channel, the opening including a circular portion and a tapered portion adjacent the circular portion, the tapered portion having a maximum width that is less than a diameter of the circular portion, wherein the valve is rotatable about a central axis of the valve to adjust a position of a cross-sectional area of the opening with respect to a cross-sectional area of an inlet fluid line positioned to deliver the fluid to the rotary valve.

Embodiments may include one or more of the following features.

In some embodiments, the circular portion of the interior channel is a through channel that extends from a first side of the valve to a second side of the valve that is opposite to the first side.

In certain embodiments, the tapered portion extends from the first side of the valve and terminates at a location internal to the valve.

In some embodiments, the opening is a first opening disposed along the first side of the valve, the valve further including a second opening disposed along the second side of the valve.

In certain embodiments, the valve is rotatable to a first rotatable position in which the cross-sectional area of the inlet fluid line is aligned with the circular portion and is offset from of the tapered portion of the interior channel to permit a maximum fluid flow rate into the interior channel.

In some embodiments, the valve is rotatable to a second rotatable position in which the cross-sectional area of the inlet fluid line is offset from the cross-sectional area of the interior channel to prevent fluid flow into the interior channel.

In certain embodiments, a flow rate of the fluid increases from zero at the second rotational position of the valve to the maximum flow rate as the valve is rotated from the second rotational position to the first rotational position.

In some embodiments, an axis of the opening is perpendicular to the central axis of the valve.

In certain embodiments, the opening is a first opening, the fluid is a first fluid, and the inlet fluid line is a first inlet fluid line, the valve further including a second opening to the interior channel that is circumferentially offset from the first opening.

In some embodiments, the valve is rotatable to adjust a position of a cross-sectional area the second opening with respect to a cross-sectional area of the second inlet fluid line positioned to deliver a second fluid to the rotary valve to control a ratio at which the first and second fluids are mixed within the interior channel.

In another aspect, a medical system includes a medical fluid pumping machine including an actuator and a valve configured to be secured to the medical fluid pumping machine such that the valve is operable with the actuator. The valve includes a valve body rotatable about a central axis of the valve body, an interior channel adjacent the valve body for permitting a fluid to flow through an axial opening of the interior channel, and a plug within the interior channel that is movable between a first axial position at the axial opening and a second axial position spaced apart from the axial opening. In the first axial position, the plug closes the axial opening to prevent the fluid from flowing through the axial opening in a first direction and to prevent the fluid from flowing through the axial opening in a second direction that is opposite to the first direction. In the second axial position, the plug permits the fluid to flow through the axial opening into the interior channel in the first direction.

Embodiments may include one or more of the following features.

In some embodiments, the medical fluid pumping machine is a dialysis machine.

In certain embodiments, the medical fluid pumping machine further includes a disposable medical fluid line set that includes the valve.

In some embodiments, the medical fluid pumping machine further includes a disposable medical fluid cassette that includes the valve.

In certain embodiments, the valve body defines an interface at which the valve is engageable with the actuator and by which the valve is rotatable by the actuator.

In some embodiments, a shape of the interface is complementary to a shape of the actuator.

In another aspect, a medical system includes a medical fluid pumping machine including an actuator and a valve configured to be secured to the medical fluid pumping machine such that the valve is operable with the actuator. The valve includes an interior channel for permitting a fluid to flow through the valve and an opening to the interior channel, the opening including a circular portion and a tapered portion adjacent the circular portion, the tapered portion having a maximum width that is less than a diameter of the circular portion, wherein the valve is rotatable about a central axis of the valve to adjust a position of a cross-sectional area of the opening with respect to a cross-sectional area of an inlet fluid line positioned to deliver the fluid to the rotary valve.

Embodiments may include one or more of the following features.

In some embodiments, the medical fluid pumping machine is a dialysis machine.

In certain embodiments, the medical system further includes a disposable medical fluid line set that includes the valve.

In some embodiments, the medical system further includes a disposable medical fluid cassette that includes the valve.

In certain embodiments, the valve body defines an interface at which the valve is engageable with the actuator and by which the valve is rotatable by the actuator.

In some embodiments, a shape of the interface is complementary to a shape of the actuator.

Embodiments may provide one or more of the following advantages.

In some embodiments, owing to a capability of the rotary valve to be adjusted for selective fluid flow in reverse directions across the rotary valve, a design of a medical system including the rotary valve can be simplified to include a fewer total number of valves relative to conventional medical systems that require a dedicated valve for flowing fluid in each of the reverse directions. In certain embodiments, owing to a capability of the rotary valve to be adjusted for selectively changing a cracking pressure, a design of a medical system including the rotary valve can be simplified to include a fewer total number of valves relative to conventional medical systems requiring dedicated valves associated with fixed cracking pressures. In some embodiments, owing to a capability of the rotary valve to be selectively enabled for permitting fluid flow in one direction or disabled for permitting fluid flow in two, reverse directions, a design of a medical system including the rotary valve can be simplified to include a fewer total number of valves relative to conventional medical systems that require dedicated check valves for limiting fluid flow to one direction and dedicated bi-directional flow valves for permitting fluid flow in opposite directions.

In certain embodiments, owing to a capability of the rotary valve to be adjusted for selectively controlling fluid flow rates and mixing ratios, a design of a medical system including the rotary valve can be simplified to include a fewer total number of valves relative to conventional medical systems that require a dedicated arrangement of valves and fluid flow lines for controlling fluid flow rates within given fluid flow lines. In some embodiments, a capability of the rotary valve to be adjusted for selective, automated control of fluid mixing can eliminate the need for manual preparation of dialysate fluid and therefore reduce a potential of errors in dialysate fluid composition that may otherwise occur with manual preparation. For example, utilizing a rotary valve in this manner to control fluid mixing may be useful for mixing dry chemical pellets with respective amounts of water in predetermined ratios for creating a dialysate fluid of a required composition.

In some embodiments, a reduced number of valves in association with any of the above-discussed rotary valves may simplify other features of a medical system, such as a fluid flow line arrangement, a valve actuator configuration, and valve control algorithms such that the medical system can operate in a robust manner. Other aspects, features, and advantages will be apparent from the description, the drawings, and the claims.

DESCRIPTION OF DRAWINGS

FIG. 1 is a perspective view of a rotary valve positioned to allow fluid flow through the rotary valve and in a first direction across the rotary valve.

FIG. 2 is a perspective view of the rotary valve of FIG. 1 positioned to allow fluid flow through the rotary valve and in a second, opposite direction across the rotary valve.

FIG. 3 is a cross-sectional view of the rotary valve of FIG. 1 positioned in the orientation shown in FIG. 1 and within a medical system.

FIG. 4 is a cross-sectional view of the rotary valve of FIG. 1 positioned in the orientation shown in FIG. 2 and within the medical system of FIG. 3.

DETAILED DESCRIPTION

Figure 6:
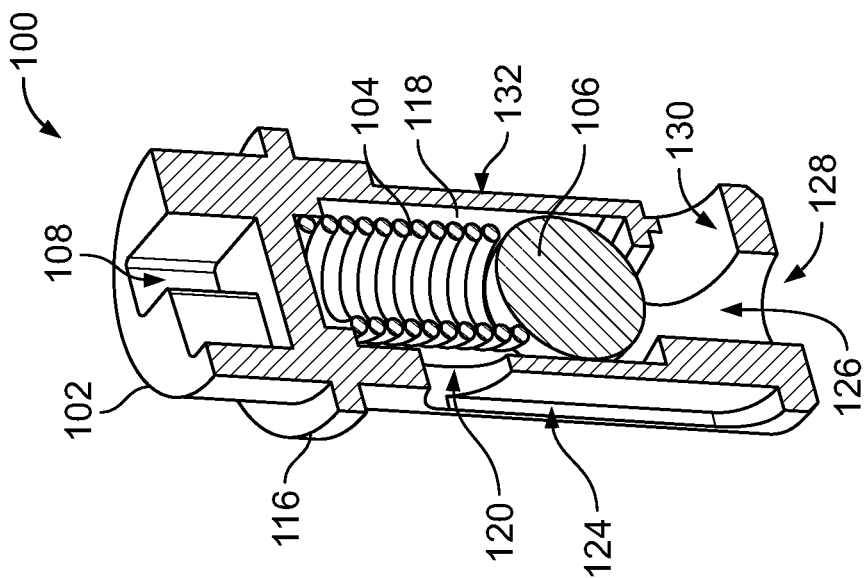
FIG. 6 is a perspective, cross-sectional view of the rotary valve of FIG. 1 positioned in the orientation shown in FIG. 2.
Figure 5:
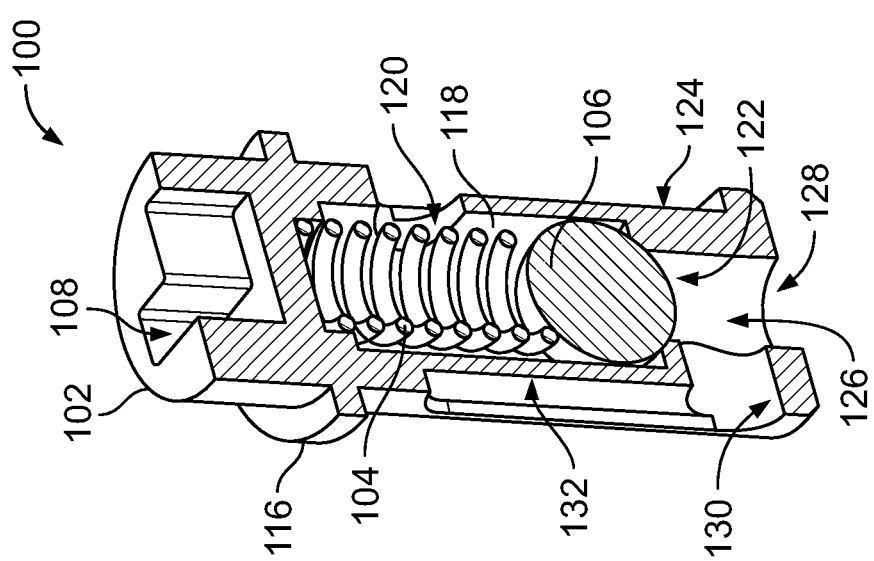
FIG. 5 is a perspective, cross-sectional view of the rotary valve of FIG. 1 positioned in the orientation shown in FIG. 1.
Figure 7:
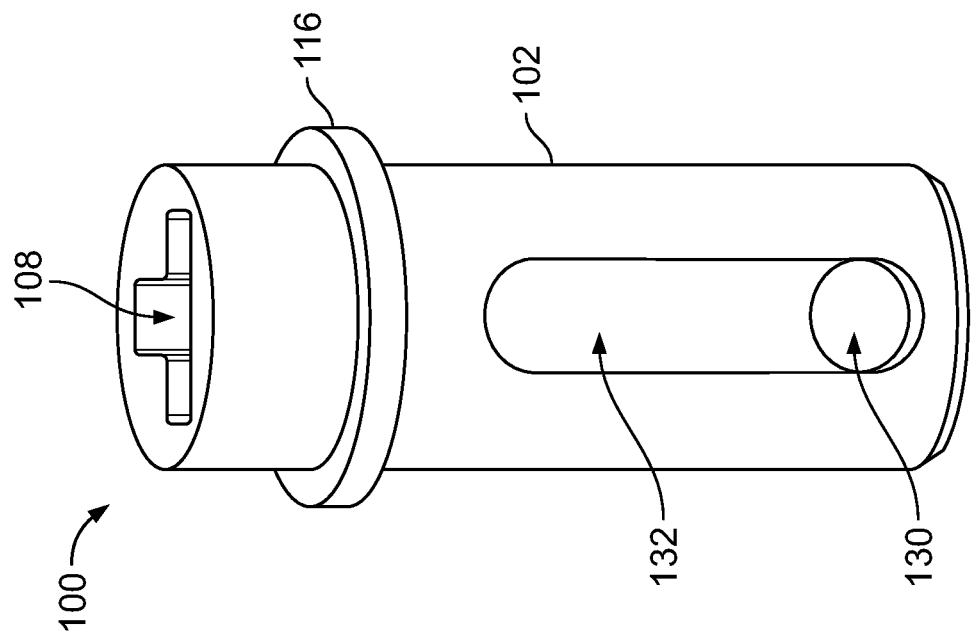
FIG. 7 is a perspective side view of a first side of the rotary valve of FIG. 1.
Figure 8:
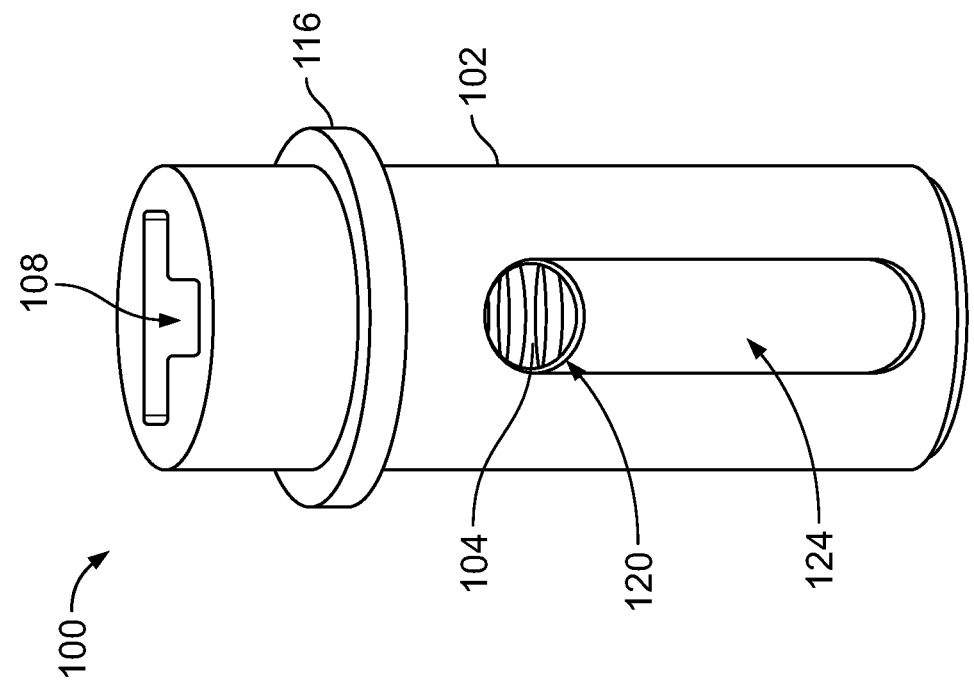
FIG. 8 is a perspective side view of a second side of the rotary valve of FIG. 1.

FIGS. 1-8 illustrate various views of a rotary valve 100 that is designed to allow fluid flow through the rotary valve 100 in a single direction 112 (e.g., a bulk flow direction) through the rotary valve or in a single, opposite direction 134 (e.g., a bulk flow direction) across the rotary valve 100. The rotary valve 100 may be a component of a medical system 101 (e.g., a dialysis system) in which a medical fluid (e.g., dialysate) is flowed in a controlled manner through various fluid lines, such as fluid lines 103, 105. The rotary valve 100 includes a valve body 102, a spring 104 housed within the valve body 102, and a ball bearing 106 housed within the valve body 102.

The valve body 102 is generally cylindrical in shape and defines an interface 108 at which the rotary valve 100 can be engaged by a system actuator (not shown) for rotating the rotary valve 100 about a central axis 110 of the valve body 102. The interface 108 is formed as a receptacle (e.g., a recessed surface) with a shape that is complimentary to that of the system actuator and that indicates a fluid flow direction. For example, the interface 108 has a "t" shape with a central extension 114 that can be oriented parallel to the first fluid flow direction 112 across the rotary valve 100 or oriented parallel to the second, opposite fluid flow direction 134 across the rotary valve 100. The valve body 102 also defines a flange 116 that seats against a housing 107 of the medical system 101.

The valve body 102 further defines various features that direct fluid flow across the rotary valve 100. For example, the valve body 102 defines an interior pocket 118 that contains the spring 104 and the ball bearing 106, a lateral opening 120 to the interior pocket 118, and an axial opening 122 to the interior pocket 118. The valve body 102 further defines an exterior channel 124 in fluid communication with and extending perpendicular to an axis of the lateral opening 120. The valve body 102 also defines an interior channel 126 extending from the axial opening 122 in the interior pocket 118 to a central opening 128 along the central axis 110 of the valve body 102. The valve body 102 further defines a lateral opening 130 extending perpendicularly from the interior channel 126, and an exterior channel 132 in fluid communication with and extending perpendicularly to an axis of the lateral opening 130.

Referring particularly to FIGS. 3-6, the spring 104 is biased to an extended configuration that forces the ball bearing 106 to a position in which the ball bearing 106 abuts the axial opening 122 of the interior pocket 118. A diameter of the ball bearing 106 is larger than a diameter of the axial opening 122 such that the ball bearing 106 closes (e.g., fluidically seals) the axial opening 122 to any fluid flowing towards the axial opening 122 when the spring 104 is in the extended configuration. In this manner, the ball bearing 106 acts as a plug within the interior pocket 118 that can prevent or permit fluid flow through the axial opening 122.

For fluid to flow through the rotary valve 100, fluid must flow into the lateral opening 130, into the interior channel 126, and towards the axial opening 122 with a pressure great enough (e.g., a cracking pressure) to push the ball bearing 106 up from the axial opening 122 (e.g., thereby compressing the spring 104) such that the fluid unseats the ball bearing 106 to allow fluid to flow from the interior channel 126 up into the interior pocket 118. The diameter of the ball bearing 106 is smaller than a diameter of the interior pocket 118 such that fluid can flow up and around the ball bearing 106 within the interior pocket 118 and out of the lateral opening 120. If fluid was to flow from the fluid line 105 and into the interior pocket 118 through the lateral opening 120, such fluid would urge the ball bearing 106 toward the axial opening 122, thereby seating the ball bearing 106 in the axial opening 122 and preventing fluid from flowing out of the interior pocket 118 through the axial opening 122. Accordingly, the spring 104, the ball bearing 106, and the interior pocket 118 together form a check valve configuration that allows fluid to flow only in a single bulk direction 160 along the central axis 110 of the valve body 102, which is transverse to the flow directions 112, 134. For example, while molecules of the fluid can flow in several different directions as the fluid travels around the ball bearing 106, a bulk direction of the fluid flow is that of the bulk flow direction 160. The check valve configuration of the rotary valve 100 typically has a cracking pressure in a range of about 500 Pa to about 10,000 Pa.

Still referring to FIGS. 3-6, the rotary valve 100 can be adjusted to a first rotational position (shown in FIGS. 3 and 5) that allows fluid to flow only in the first direction 112 from the fluid line 103 to the fluid line 105 and to a second rotational position (shown in FIGS. 4 and 6) that allows fluid to flow only in the second direction 134 from the fluid line 105 to the fluid line 103. In the first rotational position of the rotary valve 100, the fluid line 103 is axially aligned with the lateral opening 130, and the housing 107 closes off the exterior channel 132 along a circumference of the valve body 102. Similarly, the fluid line 105 is axially aligned with the lateral opening 120, and the housing 107 closes off the exterior channel 124 along the circumference of the valve body 102. Accordingly, the lateral opening 130, the interior channel 126, the axial opening 122, the interior pocket 118, and the lateral opening 120 together and sequentially form a first flow path within the rotary valve 100 along which fluid can flow in the first direction 112 across the rotary valve 100 and in the bulk direction 160 along the central axis 110.

In the second rotational position of the rotary valve 100, the fluid line 103 is aligned with a lower end of the exterior channel 124, and the housing 107 defines a flow path along the exterior channel 124 and along the circumference of the valve body 102. Similarly, the fluid line 105 is aligned with an upper end of the exterior channel 132, and the housing 107 defines a flow path along the exterior channel 132 and along the circumference of the valve body 102. Accordingly, the exterior channel 132, the lateral opening 128, the interior channel 126, the axial opening 122, the interior pocket 118, the lateral opening 120, and the exterior channel 124 together and sequentially form a second flow path within the rotary valve 100 along which fluid can flow in the second direction 134 across the rotary valve, while still flowing in the bulk direction 160 along the central axis 110. Accordingly, fluid flows in only the single bulk direction 160 along the central axis 110 of the rotary valve 100 within both the first and second flow paths.

The interior pocket 118 of the valve body 102 typically has a diameter of about 6.4 mm to about 6.8 mm (e.g., about 6.6 mm). The axial opening 122 in the interior pocket 118 typically has a diameter of about 3.9 mm to about 4.3 mm (e.g., about 4.1 mm). The ball bearing 106 typically has a diameter of about 6.1 mm to about 6.5 mm (e.g., about 6.3 mm). The lateral openings 120, 130 typically have a diameter of about 3.6 mm to about 4.0 mm (e.g., about 3.8 mm). The exterior channels 124, 132 typically have a length of about 15.3 mm to about 15.7 mm (e.g., about 15.5 mm) and a thickness of about 0.7 mm to about 1.2 mm (e.g., about 1.0 mm). The valve body 102 typically has an exterior diameter (e.g., excluding the flange 116) of about 10.0 mm to about 10.4 mm (e.g., about 10.2 mm) and a total height of about 26.5 mm to about 26.9 mm (e.g., about 26.7 mm). The flange 116 is typically spaced from an upper end of the valve body 102 by a distance of about 4.9 mm to about 5.3 mm (e.g., about 5.1 mm).

The valve body 102, the spring 104, and the ball bearing 106 are made of materials that are corrosion resistant, bio-compatible, durable, and suitable for manufacturing. For example, the valve body 102 is typically made of polyetherimide, the spring 104 is typically made of stainless steel, and the ball bearing 106 is typically made of stainless steel. Furthermore, the valve body 102 and the ball bearing 106 are typically manufactured respectively via injection molding and grinding/lapping.

Due to a capability of the rotary valve 100 to be adjusted for selective fluid flow in reverse directions 112, 134 across the rotary valve 100, a design of a medical system (e.g., a dialysis system) including the rotary valve 100 can be simplified to include a fewer total number of valves relative to conventional medical systems that require a dedicated valve for flowing fluid in each of the reverse directions. The reduced number of valves may simplify other features of the medical system, such as a fluid flow line arrangement, a valve actuator configuration, and valve control algorithms such that the medical system can operate in a robust manner.

In operation, the interface 108 on the valve body 102 can be engaged (e.g., urged) by an actuator of the medical system 101 to rotate (e.g., spin) the rotary valve 100 about the central axis 110. For example, during a fill phase of a peritoneal dialysis treatment in which a peritoneal lateral channel of a patient is filled with fresh dialysate, the rotary valve 100 may be oriented in the first rotational position to ensure that fluid flows only in the first direction 112 from the medical system 101 toward the patient. Conversely, during a drain phase of the peritoneal dialysis treatment in which the peritoneal lateral channel of the patient is drained (e.g., emptied) of used (e.g., spent) dialysate, the rotary valve 100 may be oriented in the second rotational position to ensure that fluid flows only in the second direction 134 from the patient toward the medical system 101.

Figure 9:
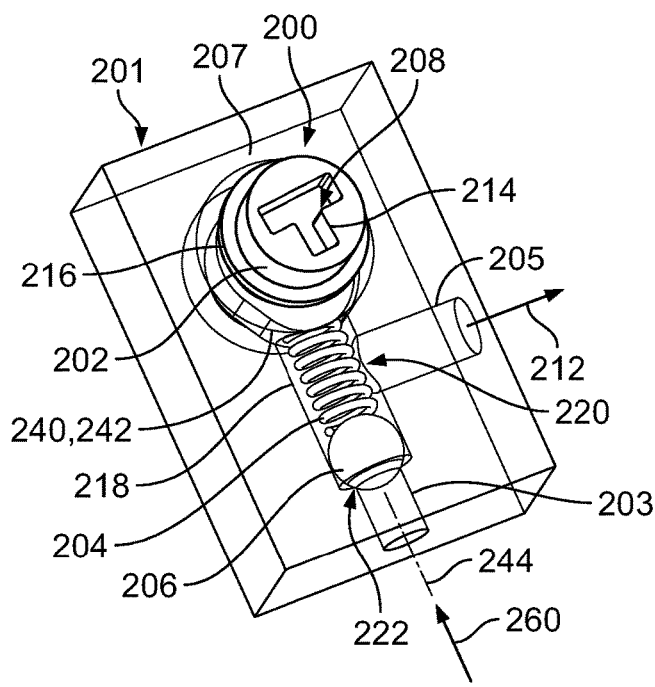
FIG. 9 is a perspective view of a rotary valve with an adjustable cracking pressure in a configuration that permits fluid flow through the rotary valve.
Figure 10:
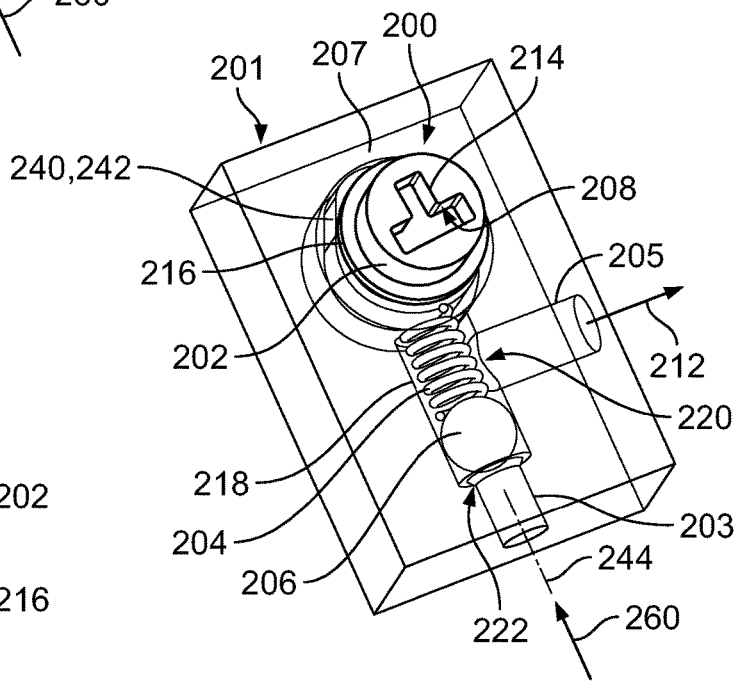
FIG. 10 is a perspective view of the rotary valve of FIG. 9 in a configuration that prevents fluid flow through the rotary valve.
Figure 11:
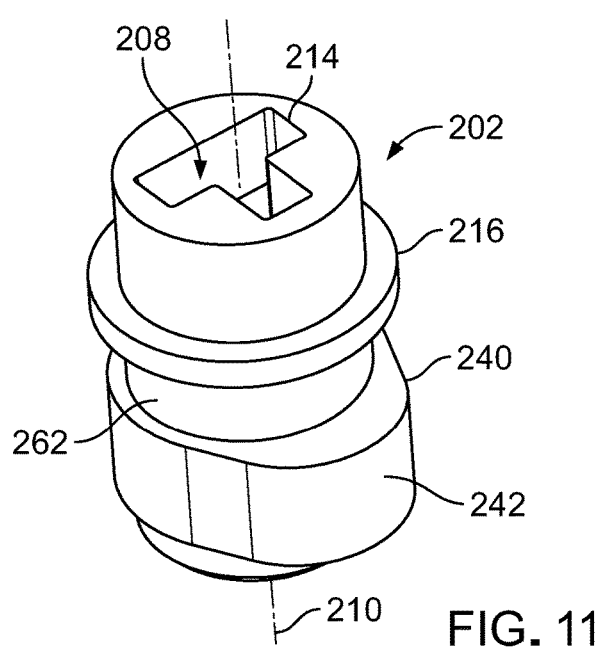
FIG. 11 is a perspective view of a valve body of the rotary valve of FIG. 9.

In some embodiments, a check valve configuration of a rotary valve may have an adjustable cracking pressure. For example, FIGS. 9-11 illustrate various views of a rotary valve 200 with an adjustable cracking pressure that is designed to allow fluid flow through the rotary valve 200 in a single direction 212 across the rotary valve 200. The rotary valve 200 may be a component of a medical system 201 (e.g., a dialysis system) in which a medical fluid (e.g., dialysate) is flowed in a controlled manner through various fluid lines, such as fluid lines 203, 205. The rotary valve 200 includes a valve body 202, a shaft 218 adjacent the valve body 202, a spring 204 housed within the shaft 218, and a ball bearing 206 housed within the shaft 218.

A central portion 262 of the valve body 202 is generally cylindrical in shape and defines an interface 208 at which the rotary valve 200 can be engaged by a system actuator (not shown) for rotating the rotary valve 200 about an axis 210 of the valve body 202. The interface 208 is formed as a receptacle (e.g., a recessed surface) with a shape that is complimentary to that of the system actuator. The valve body 202 also defines a flange 216 that seats against a housing 207 of the medical system 201 and a cam 240 of variable radius. The cam 240 is sized to compress the spring 204 to a maximum extent within the shaft 218 when a protrusion 242 of the cam 240 is aligned with an axis 244 of the shaft 218 and in contact with the spring 204. A central extension 214 of the "t" shaped interface 208 is oriented parallel to the protrusion 242 of the cam 240, such that the interface 208 provides a visual indicator of a rotational position of the cam 240 (e.g. corresponding to a rotational position of the rotary valve 200, itself).

The spring 204 is biased to an extended configuration that forces the ball bearing 206 to a position in which the ball bearing 206 abuts an axial opening 222 of the shaft 218. A diameter of the ball bearing 206 is larger than a diameter of the axial opening 222 such that the ball bearing 206 closes (e.g., fluidically seals) the axial opening 222 to fluid flow towards the axial opening 222 when the spring 204 is in the extended configuration.

For fluid to flow through the rotary valve 200, fluid must flow within the fluid line 203 towards the axial opening 122 with a pressure great enough (e.g., a cracking pressure) to push the ball bearing 206 up from the axial opening 222 (e.g., thereby compressing the spring 204) such that the fluid unseats the ball bearing 206 to allow fluid to flow from the fluid line 203 into the shaft 218. As discussed above with respect to the rotary valve 100, the diameter of the ball bearing 206 is smaller than an interior diameter of the shaft 218 such that fluid can flow up and around the ball bearing 206 within the shaft 218, out of a lateral opening 220 in the shaft 218, and into the fluid line 205. If fluid was to flow from the fluid line 205 and into the shaft 218 through the lateral opening 220, such fluid would urge the ball bearing 206 toward the axial opening 222 of the shaft 218, thereby seating the ball bearing 206 in the axial opening 222 and preventing fluid from flowing out of the shaft 218 through the axial opening 222. Accordingly, the spring 204, the ball bearing 206, and the shaft 218 together form a check valve configuration that allows fluid to flow only in a single direction 212 across the rotary valve 200 and in a single bulk direction 260 along the axis 244 of the shaft 218.

The cracking pressure required to unseat the ball bearing 206 from the axial opening 222 can be adjusted by rotating the cam 240 (e.g., by rotating the valve body 202 that defines the cam 240). For example, the cracking pressure can be adjusted to a maximum value when the protrusion 242 of the cam 240 is axially aligned with and in contact with the spring 204 such that the spring 204 is maximally compressed (as shown in FIG. 9). Conversely, the cracking pressure can be adjusted to a minimum value when the protrusion 242 of the cam 240 is axially aligned with and spaced apart from the spring 204 (e.g., facing a direction opposite the spring 204) such that the spring 204 is minimally compressed (as shown in FIG. 10). The check valve configuration of the rotary valve 200 typically has a maximum cracking pressure in a range of about [500 Pa to about 10,000 Pa and typically has a minimum cracking pressure in a range of about 500 Pa to about 1,000 Pa.

The shaft 218 typically has an interior diameter of about 6.4 mm to about 6.8 mm (e.g., about 6.6 mm) and a length of about 12.5 mm to about 12.9 mm (e.g., about 12.7 mm). The axial opening 222 in the shaft 218 typically has a diameter of about [3.9] mm to about 4.3 mm (e.g., about 4.1 mm). The ball bearing 206 typically has a diameter of about 6.1 mm to about 6.5 mm (e.g., about 6.3 mm). The lateral opening 220 typically has a diameter of about 4.9 mm to about 5.3 mm (e.g., about 5.1 mm). The central portion 262 of the valve body 202 typically has an exterior diameter of about 10.0 mm to about 10.4 mm (e.g., about 10.2 mm) and a total height of about 7.4 mm to about 7.8 mm (e.g., about 7.6 mm). The flange 216 is typically spaced from an upper end of the valve body 202 by a distance of about 4.9 mm to about 5.3 mm (e.g., about 5.1 mm). The valve body 202, the spring 204, and the ball bearing 206 are respectively made of the same materials from which the valve body 102, the spring 104, and the ball bearing 106 are made and are manufactured in the same manners.

The cam 240 is typically spaced from a lower, opposite end of the valve body 202 by a distance of about 2.3 mm to about 2.7 mm (e.g., about 2.5 mm). The cam 240 has a variable radius about the axis 210 of the valve body 102. The protrusion 242 of the cam 240 typically has a length (e.g., from a cylindrical wall of the valve body 102) of about 2.3 mm to about 2.7 mm (e.g., about 2.5 mm) and corresponds to the maximum radius of the cam 240.

Due to a capability of the rotary valve 200 to be adjusted for selectively changing a cracking pressure, a design of a medical system (e.g., a dialysis system) including the rotary valve 200 can be simplified to include a fewer total number of valves relative to conventional medical systems requiring dedicated valves associated with fixed cracking pressures. As discussed above, the reduced number of valves may simplify other features of the medical system, such as a fluid flow line arrangement, a valve actuator configuration, and valve control algorithms such that the medical system can operate in a robust manner.

In operation, the interface 208 on the valve body 202 can be engaged (e.g., urged) by an actuator of the medical system 201 to rotate (e.g., spin) the valve body 202 about the axis 210 of the valve body 202 to adjust the cracking pressure of the rotary valve 200. Adjusting the cracking pressure of the rotary valve 200 may be beneficial in cases where valves with different cracking pressures are needed. For example, a check valve can be used to regulate the fluid pressure in a system, so that the fluid pressure remains below the cracking pressure. In some embodiments of HD systems, the pressure of the dialysate fluid in the dialyzer is typically regulated.

Figure 12:
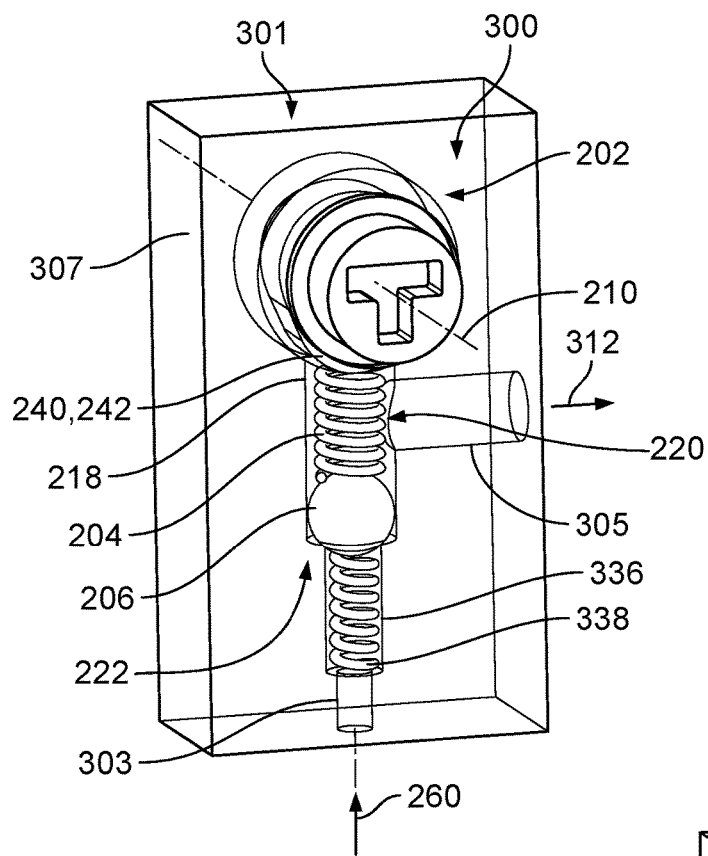
FIG. 12 is a perspective view of a rotary valve including a check valve configuration in an enabled state that prevents fluid flow through the rotary valve.
Figure 13:
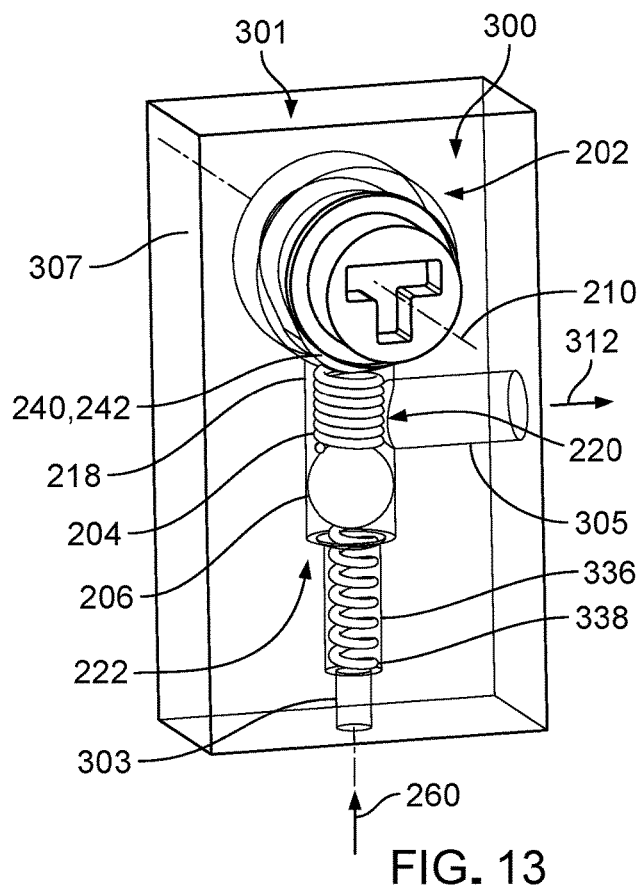
FIG. 13 is a perspective view of the rotary valve of FIG. 12 with the check valve configuration in an enabled state that permits fluid flow through the rotary valve.
Figure 14:
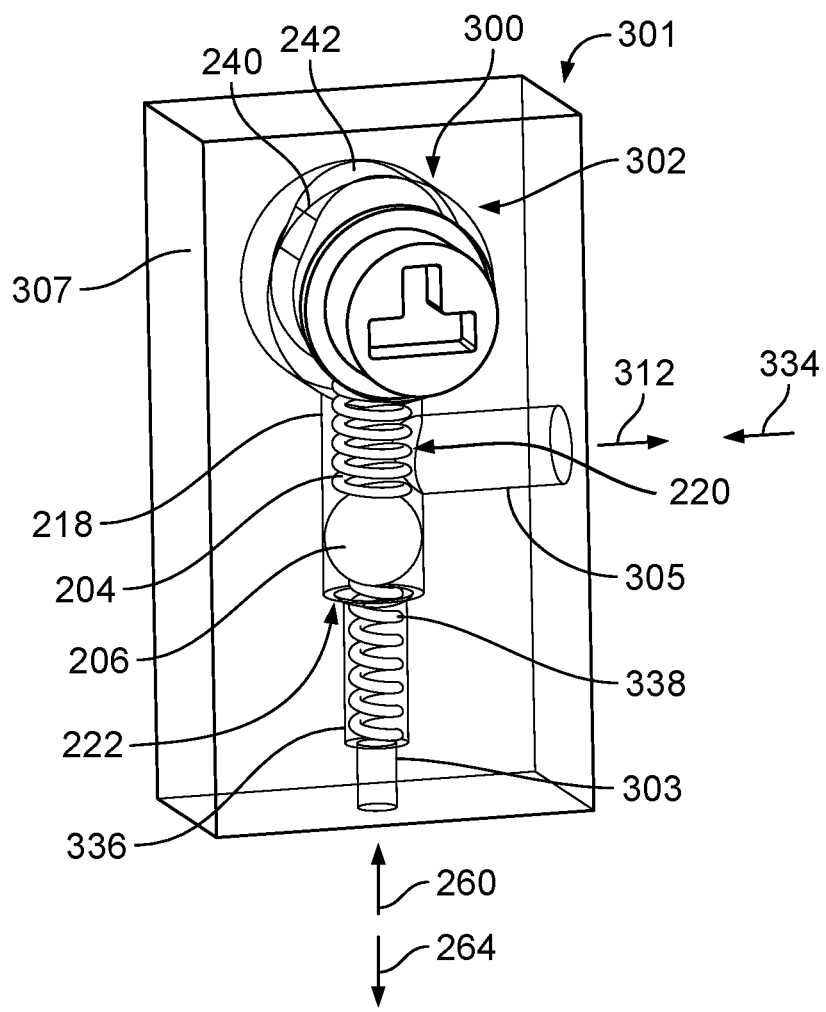
FIG. 14 is a perspective view of the rotary valve of FIG. 12 with the check valve configuration in a disabled state that permits bi-directional fluid flow through the rotary valve.
Figure 15:
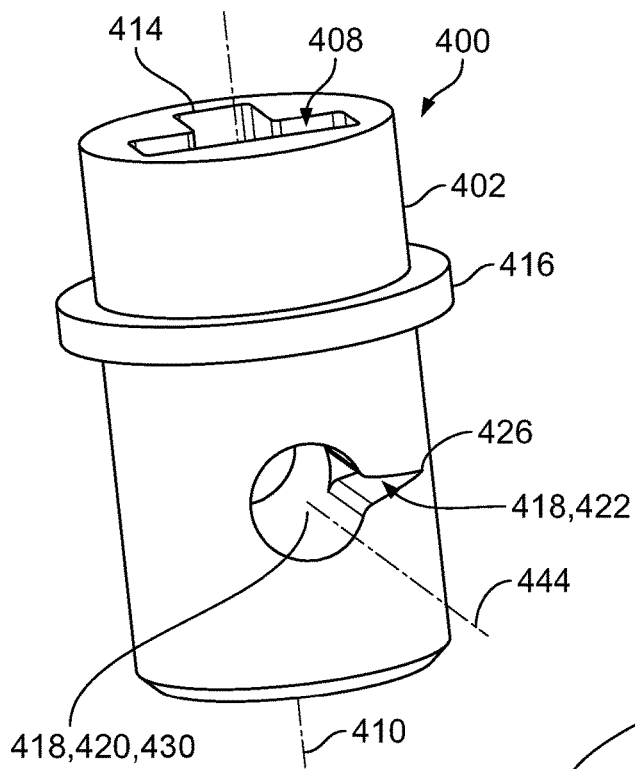
FIG. 15 is a front perspective view of a rotary valve that allows an adjustable fluid flow rate through the rotary valve.
Figure 16:
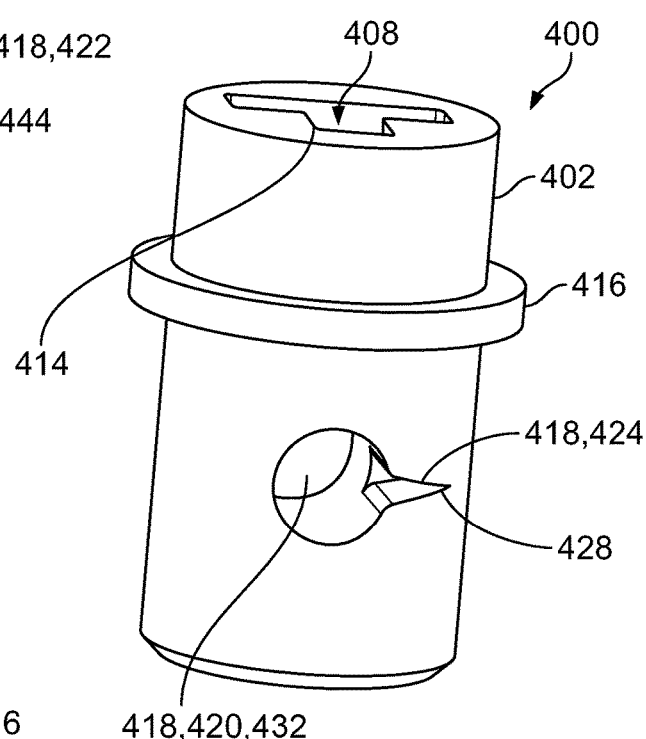
FIG. 16 is a rear perspective view of the rotary valve of FIG. 15.

In some embodiments, a check valve configuration can be enabled to permit flow in only a single bulk direction within a rotary valve and disabled to additionally permit flow in a second, reverse bulk direction within the rotary valve. For example, FIGS. 12-14 illustrate two configurations of a rotary valve 300 including such a configuration. The rotary valve 300 may be a component of a medical system 301 (e.g., a dialysis system) in which a medical fluid (e.g., dialysate) is flowed in a controlled manner through various fluid lines, such as fluid lines 303, 305.

The rotary valve 300 includes several components of the rotary valve 200 that are arranged and function as described above with respect to the rotary valve 200, such as the valve body 202, the shaft 218, the spring 204, and the ball bearing 206. The flange 216 of the valve body 202 seats against a housing 307 of the medical system 301. The rotary valve 300 further includes a shaft 336 that is axially aligned with the shaft 218 and a spring 338 contained within the shaft 336. The shaft 336 typically has an interior diameter of about 3.9 mm to about 4.3 mm (e.g., about 4.1 mm) and a length of about 9.6 mm to about 10.0 mm (e.g., about 9.8 mm).

Referring particularly to FIGS. 12 and 13, when the protrusion 242 of the cam 240 is axially aligned with and in contact with the spring 204 such that the spring 204 is maximally compressed, the spring 204, the ball bearing 206, and the shaft 218 together form a check valve configuration that allows fluid to flow in only the single bulk direction 260 along the axis 244 of the shaft 218 when the pressure of fluid flowing in the bulk direction 260 exceeds the cracking pressure of the check valve configuration, as discussed above with respect to the rotary valve 200. As long as the cracking pressure of the check valve configuration exceeds that of fluid flowing through the shaft 336 in the direction 260, the ball bearing 206 remains seated in the axial opening 222 of the shaft 218 and compresses the spring 338 such that the spring 338 is fully contained within the shaft 336, and such that fluid cannot flow through the shaft 218 in the bulk direction 260, as shown in FIG. 12.

However, once the pressure of the fluid flowing through the shaft 336 in the direction 260 exceeds the cracking pressure of the check valve configuration, the fluid unseats the ball bearing 206 to flow through the shaft 218 and out of the lateral opening 220 in a direction 312 across the rotary valve 300, and the spring 338 extends axially into the shaft 218, as shown in FIG. 13. The check valve configuration of the rotary valve 300 typically has a cracking pressure in a range of about 500 Pa to about 10,000 Pa.

Referring particularly to FIG. 14, when the protrusion 242 of the cam 240 is axially aligned with and spaced apart from the spring 204 (e.g., facing a direction opposite the spring 204) such that the spring 204 is minimally compressed, the force exerted by the spring 204 on the ball bearing 206, and therefore, the force exerted by the ball bearing 206 on the spring 338, decreases to allow the spring 338 to extend into the shaft 218 and thereby unseat the ball bearing 206 from the axial opening 222 of the shaft 218. With the ball bearing 206 unseated from the axial opening 222 and contained within the shaft 218, the spring 204, the ball bearing 206, and the shaft 218 no longer provide a check valve configuration that limits flow to only the bulk direction 260 along the shaft. Rather, fluid is permitted to flow around the ball bearing 206 within the shaft 218 bi-directionally, either in the bulk direction 260 along the axis 244 and in the direction 312 across the rotary valve 300, or in a reverse bulk direction 264 along the axis 244 and in a reverse direction 334 across the rotary valve 300 because the check valve configuration has been effectively disabled.

Due to a capability of the rotary valve 300 to be selectively adjusted for permitting fluid flow in one direction or permitting fluid flow in two, reverse directions, a design of a medical system (e.g., a dialysis system) including the rotary valve 300 can be simplified to include a fewer total number of valves relative to conventional medical systems that require dedicated check valves for limiting fluid flow to one direction and dedicated bi-directional flow valves for permitting fluid flow in opposite directions. In operation, the interface 208 on the valve body 202 can be engaged (e.g., urged) by an actuator of the medical system 301 to rotate (e.g., spin) the valve body 202 about the axis 210 of the valve body 202 to enable or disable the check valve configuration of the rotary valve 300. Enabling or disabling the check valve configuration may be useful in cases where fluid flow in a reverse direction to that of a normal operational direction is beneficial. For example, HD systems are sometimes cleaned with disinfecting fluids. In some examples, it may be beneficial for such disinfecting fluids to flow freely in a direction that is reverse to that of a normal operational direction.

In some embodiments, a rotary valve can be designed for adjusting a fluid flow rate through the rotary valve. For example, FIGS. 15-19 illustrate such a rotary valve 400. The rotary valve 400 may be a component of a medical system 401 (e.g., a dialysis system) in which a medical fluid (e.g., dialysate) is flowed in a controlled manner through various fluid lines, such as fluid lines 403, 405.

A valve body 402 of the rotary valve is generally cylindrical in shape and defines an interface 408 at which the rotary valve 400 can be engaged by a system actuator (not shown) for rotating the rotary valve 400 about an axis 410 of the valve body 402. The valve body 402 further defines an interior channel 418 and a flange 416 that seats against a housing 407 of the medical system 401. The interface 408 is formed as a receptacle (e.g., a recessed surface) with a shape that is complimentary to that of the system actuator. Furthermore, a central extension 414 of the "t" shaped interface 408 is oriented parallel to a central axis 444 of the interior channel 418.

The interior channel 418 provides a path by which fluid can flow from the fluid line 403, through the rotary valve 400, and into the fluid line 405. The interior channel 418 defines a central, cylindrical through channel 420 that defines the central axis 444. The interior channel 418 also defines two opposing lateral channels 422, 424 that open to and extend laterally from opposite sides of the through channel 420. The lateral channels 422, 424 do not extend through a complete width of the valve body 402 and therefore terminate at interior points within the valve body 402. The lateral channels 422, 424 have a generally triangular shape such that a width of the lateral channels 422, 424 increases from relatively small closed tips 426, 428 to relatively large openings 430, 432 defined by the through channel 420.

Figure 18:
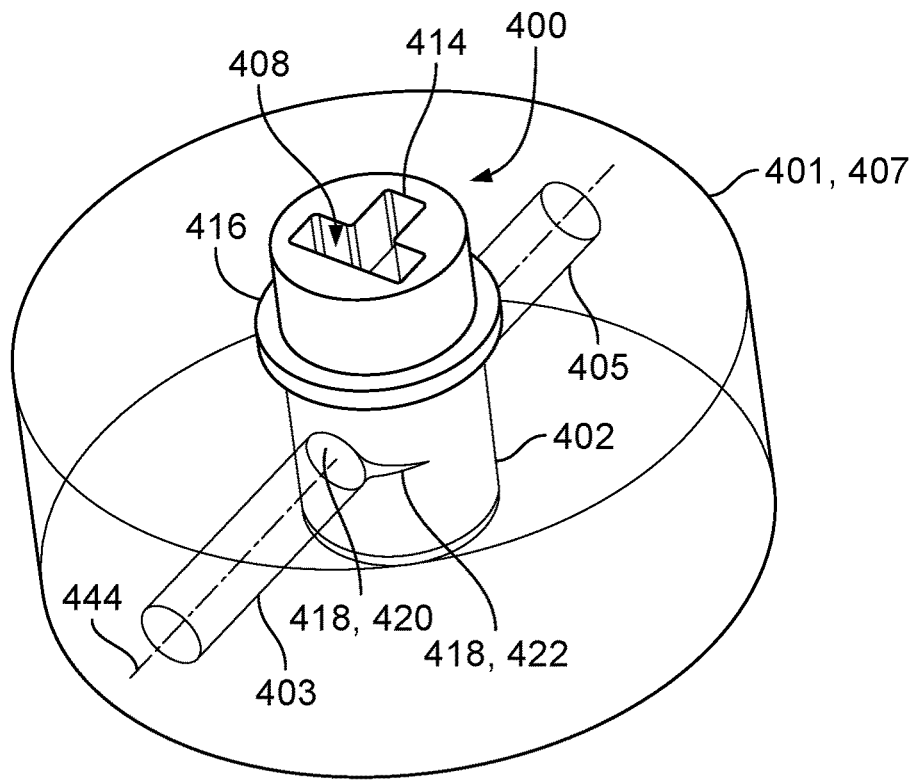
FIG. 18 is a perspective view of the rotary valve of FIG. 15 installed within a medical system in a configuration that permits maximum fluid flow through the rotary valve.

Referring particularly to FIG. 18, in a first rotational position of the rotary valve 400 in which the central axis 444 of the interior channel 418 is aligned with the fluid lines 403, 405, the rotary valve 400 achieves a maximum extent to which a cross-sectional area of the interior channel 420 (e.g., defined by a diameter of the through channel 420) can open to the fluid lines 403, 405. Thus, the rate at which fluid flows through the rotary valve 400 is maximal when the rotary valve 400 is oriented in the first rotational position.

Figure 19:
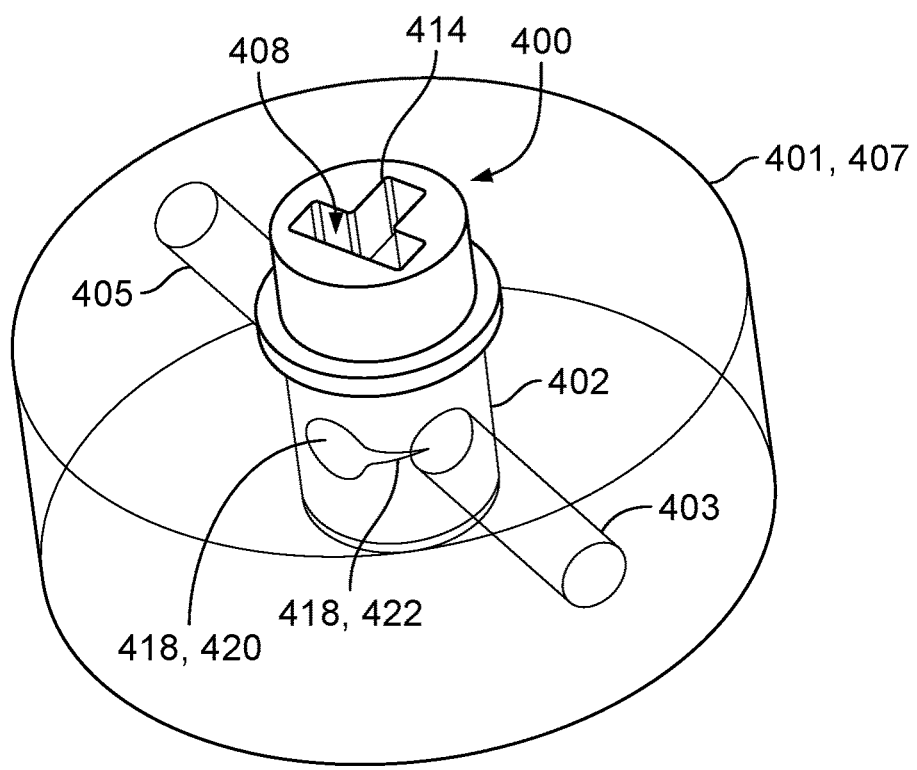
FIG. 19 is a perspective view of the rotary valve of FIG. 15 installed within the medical system of FIG. 18 in a configuration that permits reduced fluid flow through the rotary valve.

Referring particularly to FIG. 19, as the rotary valve 400 is rotated clockwise such that an opening of the through channel 420 moves away from an axis of the fluid lines 403, 405 and such that the peripheral edges of the lateral channels 422, 424 are moved to overlap the fluid lines 403, 405, the rotary valve 400 can achieve a minimum extent to which the cross-sectional area of the interior channel 420 (e.g., defined by a width of the triangular lateral channels 422, 424) opens to the fluid lines 403, 405. Thus, the rate (e.g., the non-zero rate) at which fluid flows through the rotary valve 400 is minimal when the fluid lines 403, 405 just slightly overlap the tips 426, 428 of the lateral channels 422, 424.

Figure 17:
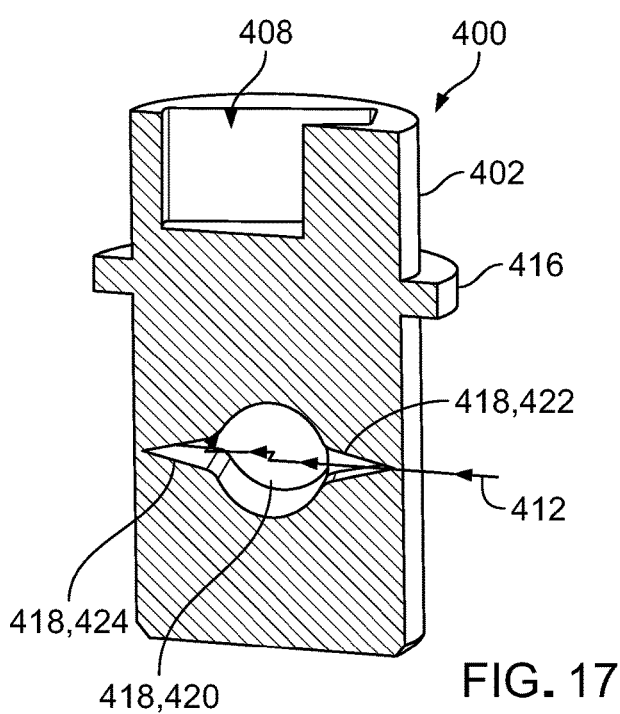
FIG. 17 is a perspective cross-sectional view of the rotary valve of FIG. 15.
Figure 20:
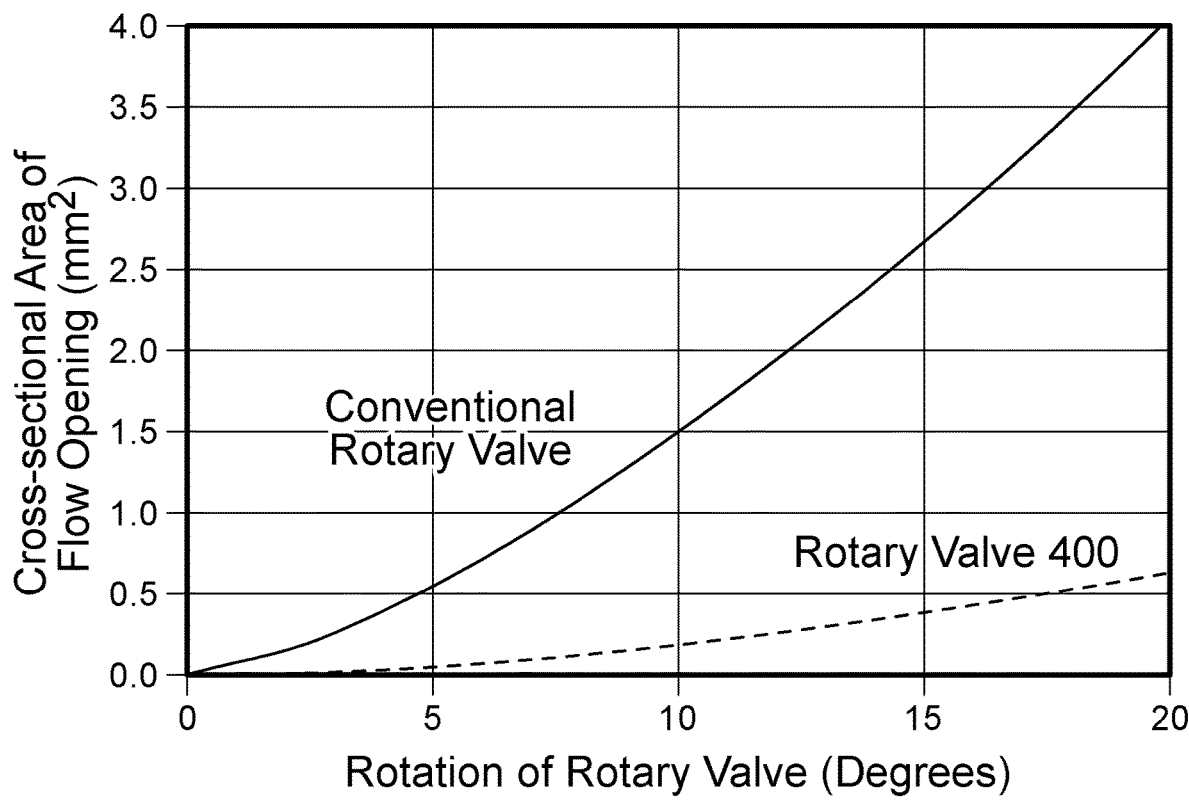
FIG. 20 is a graph that shows a cross-sectional area of a flow opening of a rotary valve as a function of a rotational position of the rotary valve, for both the rotary valve of FIG. 15 and a conventional rotary valve.

Referring particularly to FIG. 17, in such a rotational position, fluid can flow along a path 412 to sequentially flow from the fluid line 403 into the lateral channel 422, into the through channel 420, into the lateral channel 424, and into the fluid line 405 to exit the rotary valve 400. Accordingly, inclusion of the angled, winged lateral channels 422, 424 along the through channel 420 fine tunes a degree to which fluid flow rates can be controlled through the rotary valve 400. This effect is illustrated in FIG. 20, which shows a cross-sectional area of a flow opening of the interior channel 418 (e.g., including the through channel 420 and the lateral channels 422, 424) as a function of rotational position of the rotary valve 400 and of a rotary valve with simply a standard cylindrical through channel 420 (e.g., excluding lateral channels such as the lateral channels 422, 424).

The valve body 402 typically has an exterior diameter (e.g., excluding the flange 416) of about 12.5 mm to about 12.9 mm (e.g., about 12.7 mm) and a total height of about 17.6 mm to about 18.0 mm (e.g., about 17.8 mm). The flange 416 is typically spaced from an upper end of the valve body 402 by a distance of about 4.9 mm to about 5.3 mm (e.g., about 5.1 mm). The central through channel 420 typically has a diameter of about 3.6 mm to about 4.0 mm (e.g., about 3.8 mm). Each of the lateral channels 422, 424 typically has a length of about 4.1 mm to about 4.5 mm (e.g., about 4.3 mm) and a maximum width of about 1.6 mm to about 2.0 mm (e.g., about 1.8 mm). The valve body 402 is made of the same materials from which the valve body 102 is made and is manufactured via the same techniques.

Figure 21:
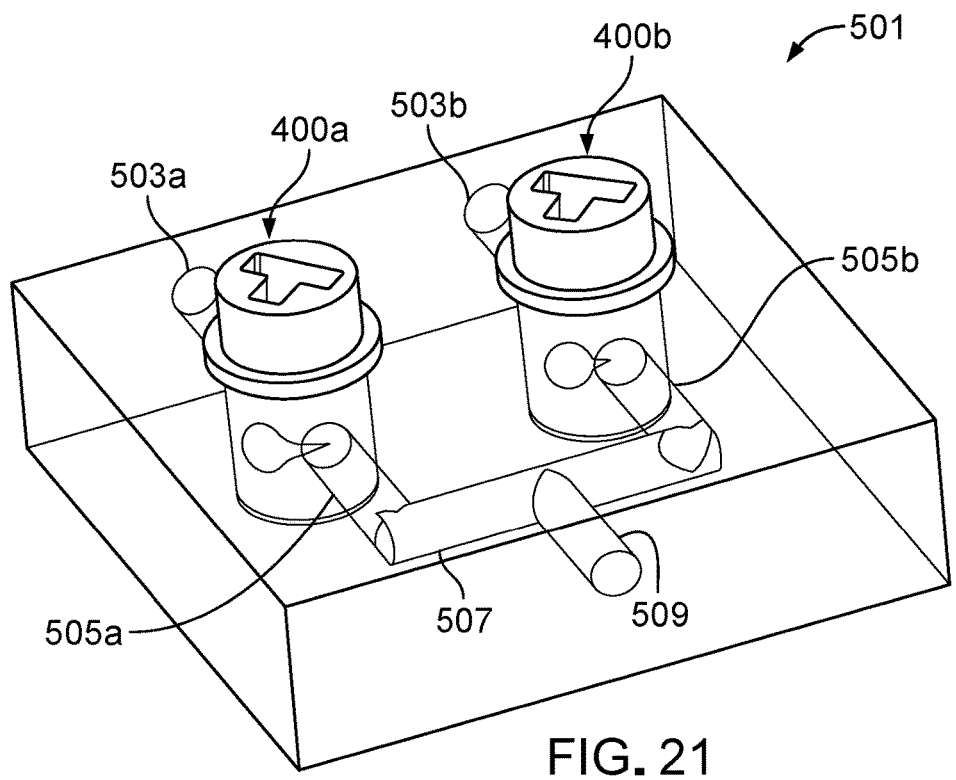
FIG. 21 is a perspective view of a medical system that includes two of the rotary valves of FIG. 15 oriented in selected rotational positions for achieving a desired fluid mixing ratio within the medical system.

FIG. 21 illustrates a medical system 501 including two of the rotary valves 400 (400a, 400b) for improving flow control when multiple inlet fluid flows are combined to provide one outlet fluid flow. For example, the medical system 501 includes inlet fluid lines 503a, 503b delivering fluid to the rotary valves 400a, 400b, subsequent intermediate fluid line 505a, 505b, a mix fluid line 507 that combines fluid flows entering through the inlet fluid lines 503a, 503b, and an outlet fluid line 509 from which a single, mixed fluid flows away from the rotary valves 400a, 400b.

A ratio at which the two entrant fluids are mixed can be controlled by selectively adjusting the rotational positions of the rotary valves 400a, 400b. For example, a rotational position of the rotary valve 400b provides a larger flow area opening to the intermediate fluid line 505b than does a rotational position of the rotary valve 400a to the intermediate fluid line 505a. Thus, the rotational position of the rotary valve 400b allows a higher fluid flow rate therethrough than does the rotational position of the rotary valve 400a.

Owing to a capability of the rotary valve 400 to be adjusted for selectively controlling fluid flow rates and mixing ratios, a design of a medical system (e.g., a dialysis system) including the rotary valve 400 can be simplified to include a fewer total number of valves relative to conventional medical systems that require a dedicated arrangement of valves and fluid flow lines for controlling fluid flow rates within given fluid flow lines. As discussed above with respect to the rotary valves 100, 200, 300, the reduced number of valves may simplify other features of the medical system, such as a fluid flow line arrangement, a valve actuator configuration, and valve control algorithms such that the medical system can operate in a robust manner. Utilizing rotary valves 400 in this manner may be useful in cases where two fluids need to be accurately mixed (e.g., for an HD system that is operated to mix water, acid/acetate, and/or bicarbonate to prepare dialysate fluid).

Figure 22:
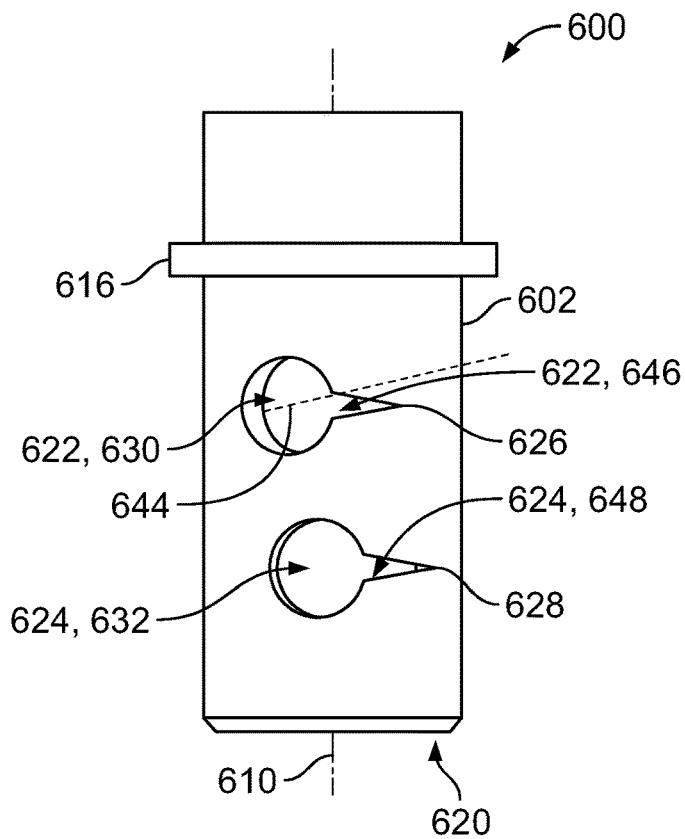
FIG. 22 is a side perspective view of a rotary valve that allows adjustable flow rates for multiple fluid flowing into the rotary valve.
Figure 23:
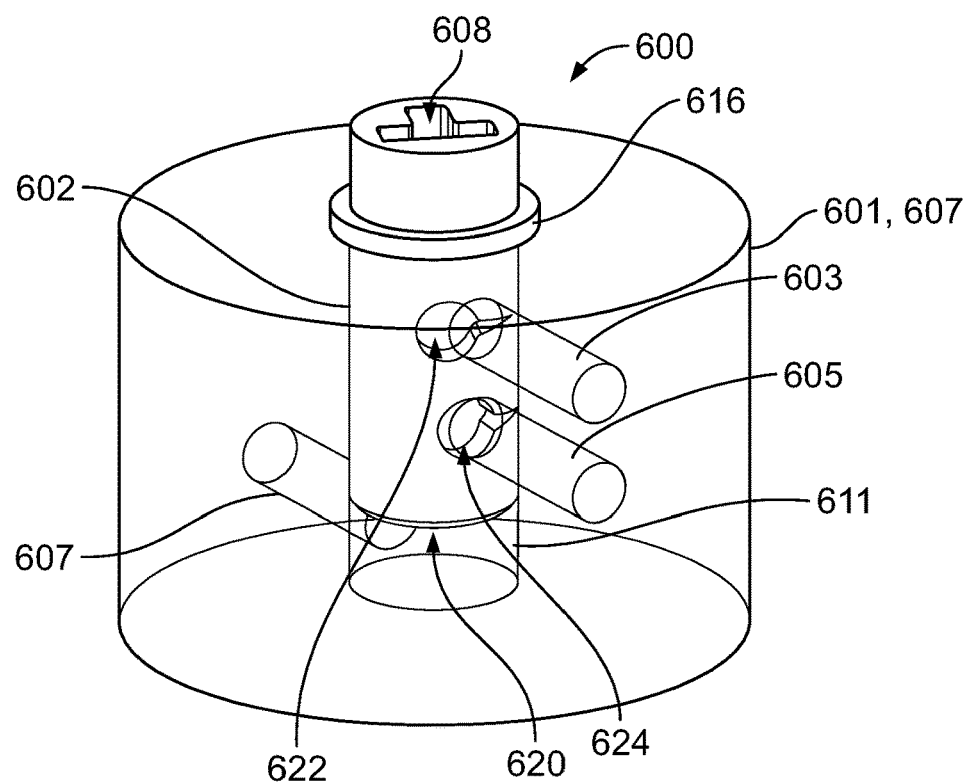
FIG. 23 is a perspective view of the rotary valve of FIG. 22 installed within a medical system.
Figure 24:
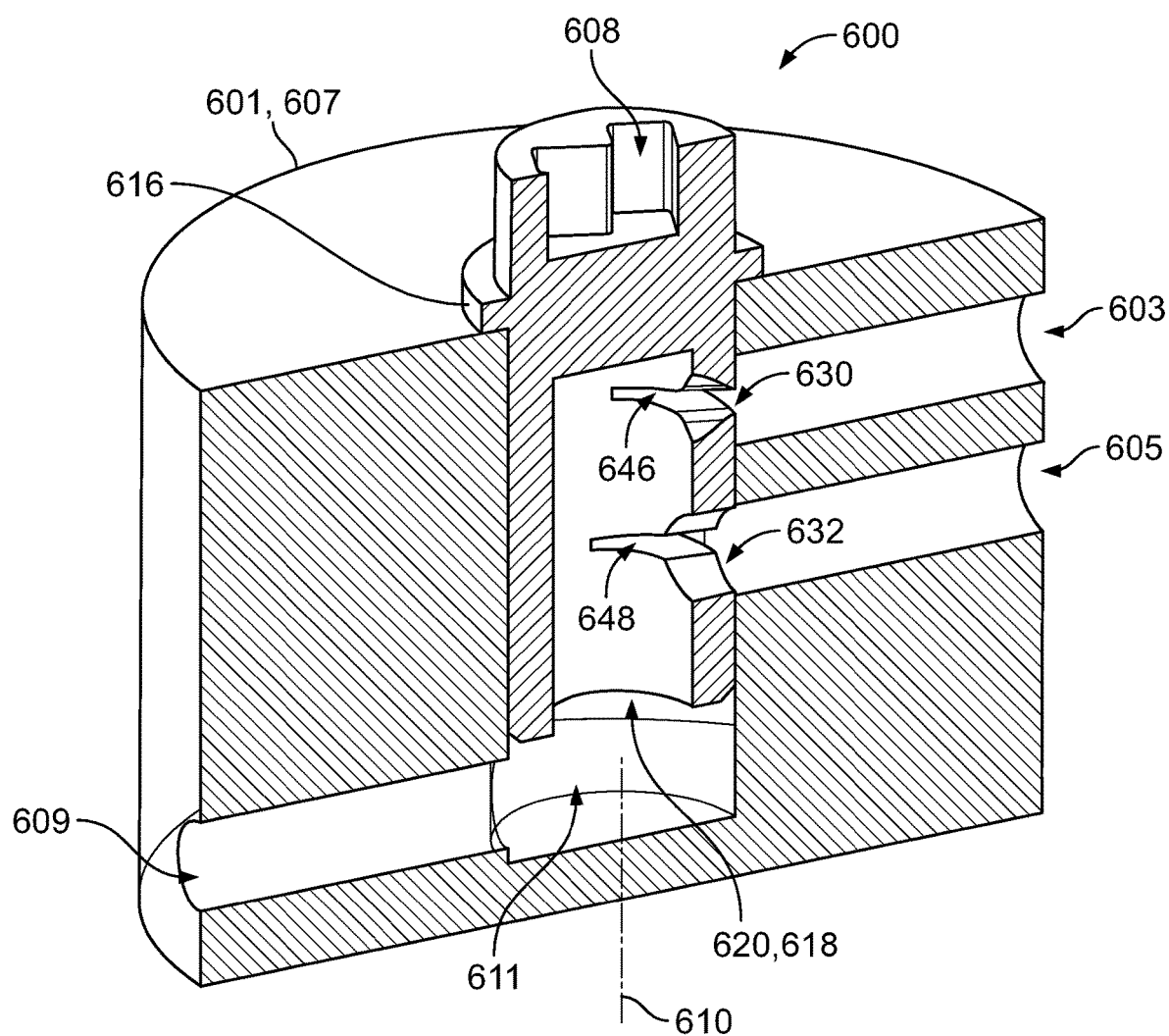
FIG. 24 is a perspective cross-sectional view of the rotary valve of FIG. 22 within the medical system of FIG. 23.

FIGS. 22-24 illustrate a rotary valve 600 designed for adjusting multiple fluid flow rates through the rotary valve 600. The rotary valve 600 may be a component of a medical system 601 (e.g., a dialysis system) in which a medical fluid (e.g., dialysate) is flowed in a controlled manner through various fluid lines, such as fluid lines 603, 605, 607.

A valve body 602 of the rotary valve is generally cylindrical in shape and defines an interface 608 and a flange 616 that are substantially similar in construction and function to the interface 408 and the flange 416 of the rotary valve 400. The valve body 602 further defines an interior channel 618 that is centered on a central axis 610 of the rotary valve 600 and that provides a fluid path by which fluid can flow from the inlet fluid lines 603, 605, through the rotary valve 600, and into the outlet fluid line 609. The valve body 602 also defines an axial opening 620 at a lower end of the interior channel 618 and two lateral openings 622, 624. The lateral openings 622, 624 respectively include cylindrical portions 630, 632 that open to triangular portions 646, 648. A width of the triangular portions 646, 648 respectively increases from relatively small closed tips 626, 628 to a maximum width along the cylindrical portions 630, 632.

Using the lateral opening 622 as an example, in a first rotational position of the rotary valve 600 in which a central axis 644 of the lateral opening 622 is aligned with that of the fluid line 603, the rotary valve 600 achieves a maximum extent to which a cross-sectional area of the lateral opening 622 (e.g., defined by a diameter of the cylindrical portion 630) can open to the fluid line 603. Thus, the rate at which fluid flows through the lateral opening 622 is maximal in the first rotational position. As the rotary valve 600 is rotated clockwise such that the cylindrical portion 630 moves away from the fluid line 603 and such that the triangular portion 646 is moved to overlap the fluid line 603, the rotary valve 600 can achieve a minimum extent to which the cross-sectional area of the lateral opening 622 (e.g., defined by a width of the triangular portion 646) opens to the fluid line 603. Thus, the rate (e.g., the non-zero rate) at which fluid flows through the lateral opening 622 is minimal when the fluid line 603 just slightly overlaps the tip 626 of the lateral opening 622. Accordingly, inclusion of the triangular portion 646 along the cylindrical portion 630 fine tunes a degree to which the fluid flow rate can be controlled through the lateral opening 622, as discussed above with respect to the interior channel 418 of the rotary valve 400. In a similar manner, the fluid flow rate can be controlled from the fluid line 605 through the lateral opening 624.

While the fluid lines 603, 605 are located at a same angular position about a circumference of the valve body 602 (as shown in FIG. 23), the lateral openings 622, 624 are located at different angular positions about the circumference of the valve body 602 (e.g., the lateral openings 622, 624 are circumferentially offset from each other, as shown in FIG. 24). Therefore, a ratio at which two entrant fluids are mixed within the interior channel 618 can be controlled by adjusting the rotational position of the rotary valve 600. In the example rotary valve 600, the lateral opening 622 is positioned clockwise of the lateral opening 624 such that at any given rotational position, fluid flows at a lower rate through the lateral opening 622 than through the lateral opening 624. The axial opening 620 of the rotary valve 600 delivers a mixed fluid to a lateral channel 611 of the housing 607 that is beneath the rotary valve 600 and that is fixed with respect to a position of the outlet fluid line 609.

Utilizing a rotary valve 600 in this manner to control fluid mixing may be useful for mixing dry chemical pellets with respective amounts of water in predetermined ratios for creating a dialysate fluid of a required composition. This capability of the rotary valve 600 to be adjusted for selective, automated control of fluid mixing can eliminate the need for manual preparation of dialysate fluid and therefore reduce a potential of errors in dialysate fluid composition that may otherwise occur with manual preparation.

The valve body 602 typically has an exterior diameter (e.g., excluding the flange 616) of about 10.0 mm to about 10.4 mm (e.g., about 10.2 mm) and a total height of about 23.9 mm to about 24.3 mm (e.g., about 24.1 mm). The flange 616 is typically spaced from an upper end of the valve body 602 by a distance of about 4.9 mm to about 5.3 mm (e.g., about 5.1 mm). The interior channel 618 (e.g., and therefore the axial opening 620) typically has a diameter of about 6.1 mm to about 6.5 mm (e.g., about 6.3 mm). The cylindrical portions 630, 632 of the lateral openings 622, 624 typically have a diameter of about 3.6 mm to about 4.0 mm (e.g., about 3.8 mm). The triangular portions 646, 648 of the lateral openings 622, 624 typically have a length of about 4.1 mm to about 4.5 mm (e.g., about 4.3 mm) and a maximum width of about 1.6 mm to about 2.0 mm (e.g., about 1.8 mm). The valve body 602 is made of the same materials from which the valve body 102 is made and is manufactured via the same techniques.

Figure 25:
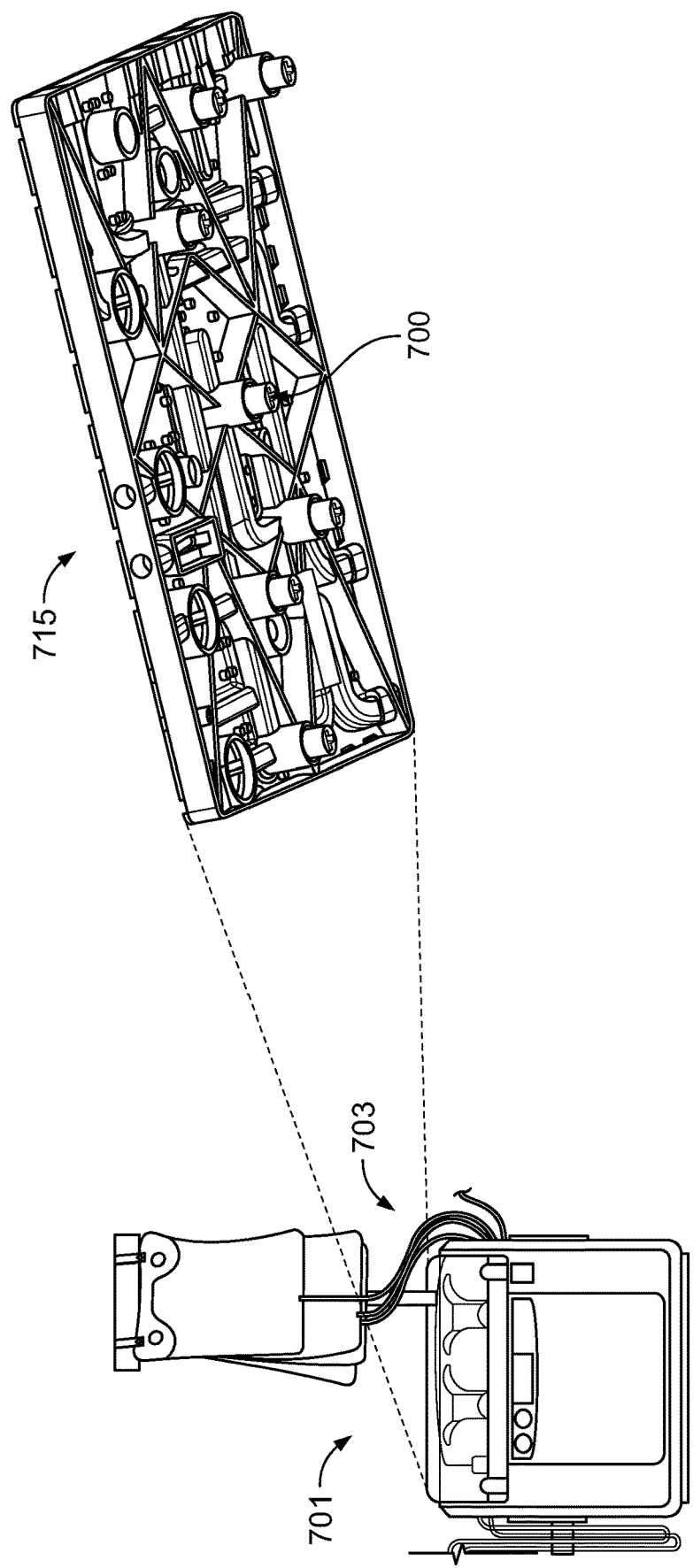
FIG. 25 is a schematic illustration of an example medical system including multiple example rotary valves that can be operated to carry out a medical treatment.

FIG. 25 illustrates an example dialysis system 701 that includes rotary valves 700. In some embodiments, the dialysis system 701 can represent several different types of systems, including but not limited to an HD system, a PD system, a hemofiltration system, a hemodiafiltration system, an apheresis system, a dialysate generation system, or a water purification system. In some embodiments, the rotary valves 700 may represent any of the above-discussed rotary valves 100, 200, 300, 400, 600. The dialysis system 701 includes an example disposable fluid cassette 715 to which the rotary valves 700 and multiple fluid lines 703 are secured. The cassette 715, the rotary valves 700, and the fluid lines 703 together form a disposable fluid line cassette. The example dialysis system 701 can be operated to carry out any of the various medical treatments described above with respect to the rotary valves 100, 200, 300, 400, 600.

While the above-discussed rotary valves 100, 200, 300, 400, 600 have been described and illustrated as including certain dimensions, sizes, shapes, and materials, in some embodiments, rotary valves that are substantially similar in structure and function to the above-discussed rotary valves 100, 200, 300, 400, 600 may include one or more different dimensions, sizes, shapes, and materials. Furthermore, while the rotary valves 100, 200, 300, 400, 600 have been described and illustrated as being positioned in certain arrangements and configurations in the medical systems 101, 201, 301, 401, 501, 601 and used in certain processes for managing medical fluids, in some embodiments, the rotary valves 100, 200, 300, 400, 600 maybe positioned in other arrangements and configurations within a medical system (e.g., such as an HD system, a PD system, a hemofiltration system, a hemodiafiltration system, an apheresis system, a dialysate generation system, or a water purification system), used in other processes for managing medical fluids, or used in other, non-medical systems for managing other types of fluids.

While the above-discussed actuator interfaces 108, 208, 308, 408, 608 have been described and illustrated as having a "t" shape, in some embodiments, a rotary valve that is substantially similar in construction and function to any of the rotary valves 100, 200, 300, 400, 600 may include an actuator interface of a different shape (e.g., either a symmetric or non-symmetric shape) for engagement with a corresponding system actuator.

Accordingly, other embodiments are within the scope of the following claims.

What is claimed is:

1. A valve, comprising:
    a valve body that is rotatable about a central axis of the valve body and that defines:
        an elongate exterior channel extending axially along an outer surface of the valve body, and
        an interior channel in fluid communication with the elongate exterior channel and extending axially within the valve body for permitting a fluid to flow through an axial opening of the interior channel; and
    a plug within the interior channel that is movable between:
        a first axial position at the axial opening in which the plug closes the axial opening to prevent the fluid from flowing through the axial opening in a first direction and to prevent the fluid from flowing through the axial opening in a second direction that is opposite to the first direction, and
        a second axial position spaced apart from the axial opening in which the plug permits the fluid to flow through the axial opening into the interior channel in the first direction.

2. The valve of claim 1, further comprising a compressible member within the interior channel that biases the plug to the first axial position.

3. The valve of claim 2, wherein the valve is configured such that the plug is movable from the first axial position to the second axial position by a pressure of the fluid flowing into the axial opening.

4. The valve of claim 1, wherein the valve defines a lateral opening in the interior channel through which fluid can flow out of the interior channel.

5. The valve of claim 4, wherein the lateral opening is in fluid communication with the elongate exterior channel.

6. The valve of claim 1, wherein the elongate exterior channel is a first elongate exterior channel extending along a first side of the valve body, and wherein the valve body further defines a second elongate exterior channel extending axially along the outer surface of a second side of the valve body that is opposite the first side, the second elongate exterior channel being fluidly communicatable with the interior channel.

7. The valve of claim 6, wherein the valve body is rotatable to:
    a first rotational position in which the fluid flows in a third direction across the valve body and past the first and second elongate exterior channels, and
    a second rotational position in which the fluid flows in a fourth direction across the valve body and along the first and second elongate exterior channels, the fourth direction being opposite to the third direction.

8. The valve of claim 1, wherein the elongate exterior channel forms at least a portion of a fluid flow path along the outer surface of the valve body.

9. A medical system, comprising:
a medical fluid pumping machine comprising an actuator; and
a valve configured to be secured to the medical fluid pumping machine such that the valve is operable with the actuator, the valve comprising:
  a valve body that is rotatable about a central axis of the valve body and that defines:
    an elongate exterior channel extending axially along an outer surface of the valve body, and
    an interior channel in fluid communication with the elongate exterior channel and extending axially within the valve body for permitting a fluid to flow through an axial opening of the interior channel, and
  a plug within the interior channel that is movable between:
    a first axial position at the axial opening in which the plug closes the axial opening to prevent the fluid from flowing through the axial opening in a first direction and to prevent the fluid from flowing through the axial opening in a second direction that is opposite to the first direction, and
    a second axial position spaced apart from the axial opening in which the plug permits the fluid to flow through the axial opening into the interior channel in the first direction.

10. The medical system of claim 9, wherein the medical fluid pumping machine is a dialysis machine.

11. The medical system of claim 9, further comprising a disposable medical fluid line set that comprises the valve.

12. The medical system of claim 9, further comprising a disposable medical fluid cassette that comprises the valve.

13. The medical system of claim 9, wherein the valve body defines an interface at which the valve is engageable with the actuator and by which the valve is rotatable by the actuator.

14. The medical system of claim 13, wherein a shape of the interface is complementary to a shape of the actuator.

15. A valve, comprising:
a valve body that is rotatable about a central axis of the valve body and that defines a cam;
a first interior channel positioned adjacent the cam of the valve body, the first interior channel permitting a fluid to flow through an axial opening of the interior channel;
a plug within the first interior channel that is movable between:
  a first axial position at the axial opening in which the plug closes the axial opening to prevent the fluid from flowing through the axial opening in a first direction and to prevent the fluid from flowing through the axial opening in a second direction that is opposite to the first direction, and
  a second axial position spaced apart from the axial opening in which the plug permits the fluid to flow through the axial opening into the first interior channel in the first direction;
a first compressible member within the first interior channel that biases the plug to the first axial position;
a second interior channel; and
a second compressible member within the second interior channel,
wherein the second interior channel and the second compressible member are positioned adjacent the plug and opposite the first interior channel and the first compressible member.

16. The valve of claim 15, wherein the valve body is rotatable to:
a first rotational position in which a protrusion of the cam is aligned with and squeezes the first compressible member into a compressed configuration that exerts a first cracking pressure on the plug, and
a second rotational position in which the protrusion of the cam is aligned with and spaced apart from the first compressible member to release the first compressible member into an extended configuration that exerts a second cracking pressure on the plug, the second cracking pressure being less than the first cracking pressure.

17. The valve of claim 15, wherein the valve body is rotatable to:
a first rotational position in which a protrusion of the cam is aligned with and squeezes the first compressible member into a compressed configuration that biases the plug to the first axial position, and
a second rotational position in which the protrusion of the cam is aligned with and spaced apart from the first compressible member to release the first and second compressible members into an extended configuration in which the second compressible member positions the plug at the second axial position to allow the fluid to flow through the axial opening in the first direction or to allow the fluid to flow through the axial opening and past the plug in the second direction.

* * * * *